US006259399B1

(12) United States Patent
Krasner

(10) Patent No.: US 6,259,399 B1
(45) Date of Patent: Jul. 10, 2001

(54) GPS RECEIVERS AND GARMENTS CONTAINING GPS RECEIVERS AND METHODS FOR USING THESE GPS RECEIVERS

(75) Inventor: Norman F. Krasner, San Carlos, CA (US)

(73) Assignee: SnapTrack, Inc., Campbell, CA (US)

( * ) Notice: Subject to any disclaimer, the term of this patent is extended or adjusted under 35 U.S.C. 154(b) by 0 days.

(21) Appl. No.: 09/132,573

(22) Filed: Aug. 11, 1998

Related U.S. Application Data

(60) Division of application No. 08/723,220, filed on Oct. 7, 1996, now Pat. No. 5,825,327, and a continuation-in-part of application No. 08/652,833, filed on May 23, 1996, now Pat. No. 6,002,363, and a continuation-in-part of application No. 08/612,669, filed on Mar. 8, 1996, now Pat. No. 5,663,774
(60) Provisional application No. 60/005,318, filed on Oct. 9, 1995.

(51) Int. Cl.[7] ............................... G01S 5/02; H04B 7/185
(52) U.S. Cl. ............................... 342/357.06; 342/357.09; 342/196
(58) Field of Search ...................... 342/357.06, 357.09, 342/196; 701/213, 215; 375/208

(56) References Cited

U.S. PATENT DOCUMENTS

| 3,823,403 | * | 7/1974 | Walter et al. | 343/708 |
| 4,445,118 | | 4/1984 | Taylor et al. | 343/357 |
| 4,578,678 | | 3/1986 | Hurd | 343/357 |
| 4,601,005 | | 7/1986 | Kilvington | 364/602 |
| 4,701,934 | | 10/1987 | Jasper | 375/1 |
| 4,785,463 | | 11/1988 | Jane et al. | 375/1 |
| 4,797,677 | | 1/1989 | MacDoran et al. | 342/352 |
| 4,879,755 | * | 11/1989 | Stolarczyk et al. | 455/3 |
| 4,881,080 | | 11/1989 | Jablonski | 342/357 |
| 4,959,656 | | 9/1990 | Kumar | 342/418 |

(List continued on next page.)

FOREIGN PATENT DOCUMENTS

| 0447978 | 9/1991 | (EP) . |
| 0545636 | 6/1993 | (EP) . |
| 2273218 | 6/1994 | (GB) . |
| WO9428434 | 12/1994 | (WO) . |

OTHER PUBLICATIONS

Henri J. Nussbaumer, "Fast Fourier Transform and Convolution Algorithms," Springer–Verlag, title page and Table of Contents (6 pages total), 1982.
Parkinson and Spilker, Jr. "Global Positioning System: Theory and Applications, vol. 1," *American Institute of Aeronautics and Astronautics, Inc.*, Chapter 5, pp. 177–208 and Table of Contents, pp. ix–xviii (1996).
PCT International Search Report mailed Feb. 21, 1997.
PCT International Search Report mailed Mar. 10, 1997.
PCT International Search Report, mailed May 13, 1997.
Davenport, Robert G., FFT Processing of Direct Sequence Spreading Codes Using Modem DSP Microprocessors, IEEE 1991 National Aerospace and Electronics Conference NAECON 1991, vol. 1, pp. 98–105, May 1991.
Rodgers, Arthur and Anson, Peter, Animal–borne GPS: Tracking the Habitat, GPS World, pp. 21–22, Jul. 1994.

(List continued on next page.)

*Primary Examiner*—Dao Phan
(74) *Attorney, Agent, or Firm*—Blakely, Sokoloff, Taylor & Zafman

(57) ABSTRACT

A GPS receiver having multiple GPS antennas. Also described is a method of tracking employing the GPS receiver and a communication transmitter. Also described is a garment having a GPS receiver and a GPS antenna and a communication antenna and a communication transmitter.

29 Claims, 17 Drawing Sheets

U.S. PATENT DOCUMENTS

| | | | |
|---|---|---|---|
| 4,998,111 | | 3/1991 | Ma et al. ............................... 342/352 |
| 5,043,736 | | 8/1991 | Darnell et al. ........................ 342/357 |
| 5,146,231 | * | 9/1992 | Ghaem et al. ........................ 342/419 |
| 5,148,002 | | 9/1992 | Kuo et al. ............................. 219/211 |
| 5,177,493 | | 1/1993 | Kawamura ............................ 343/713 |
| 5,185,610 | | 2/1993 | Ward et al. ........................... 342/357 |
| 5,202,829 | | 4/1993 | Geier .................................... 364/449 |
| 5,223,844 | | 6/1993 | Mansell et al. ....................... 342/357 |
| 5,225,842 | | 7/1993 | Brown et al. ......................... 342/357 |
| 5,245,634 | | 9/1993 | Averbuch .............................. 375/108 |
| 5,248,981 | * | 9/1993 | Yoshihara et al. ................... 342/357 |
| 5,271,034 | | 12/1993 | Abaunza ................................. 375/1 |
| 5,311,194 | | 5/1994 | Brown .................................. 342/357 |
| 5,317,323 | | 5/1994 | Kennedy et al. ..................... 342/457 |
| 5,323,163 | | 6/1994 | Maki ..................................... 342/357 |
| 5,341,301 | * | 8/1994 | Shirou et al. ......................... 364/445 |
| 5,365,450 | | 11/1994 | Schuchman et al. ................. 364/449 |
| 5,379,047 | | 1/1995 | Yokev et al. ......................... 342/457 |
| 5,379,224 | | 1/1995 | Brown et al. ......................... 364/449 |
| 5,379,320 | | 1/1995 | Fernandes et al. ...................... 375/1 |
| 5,416,797 | | 5/1995 | Gilhousen et al. ................... 375/705 |
| 5,420,592 | | 5/1995 | Johnson ................................ 342/357 |
| 5,430,759 | | 7/1995 | Yokev et al. ......................... 375/202 |
| 5,448,773 | | 9/1995 | McBurney et al. ................... 455/343 |
| 5,461,365 | * | 10/1995 | Schlager et al. ...................... 340/573 |
| 5,483,549 | | 1/1996 | Weinberg et al. .................... 375/200 |
| 5,491,486 | | 2/1996 | Welles, II et al. .................... 347/357 |
| 5,636,123 | * | 6/1997 | Rich et al. ............................ 364/461 |
| 5,663,733 | * | 9/1997 | Lennen ................................. 342/357 |

OTHER PUBLICATIONS

RCTM Recommended Standards for Differential NAVSTAR GPS Service, Version 2.0, Radio Technical Commission for Maritime Services, Jan. 1, 1990.

Peterson, Benjamin et al., GPS Receiver Structures for the Urban Canyon, ION–GPS–95, Session C4, Land Vehicular Applications, Palm Springs, CA Sep. 1995.

F.H. Rabb, et al., An Application of the Global Positioning System to Search and Rescue and Remote Tracking, Navigation: Journal of the Institute of Navigation, vol. 25, No. 3, Fall 1977.

NAVSTAR GPS User Equipment, Introduction, NATO, Feb. 1991.

Navigation: Journal of the Institute of Navigation, vol. 25, No. 2, The Institute of Navigation, Summer 1978 (entire edition).

* cited by examiner

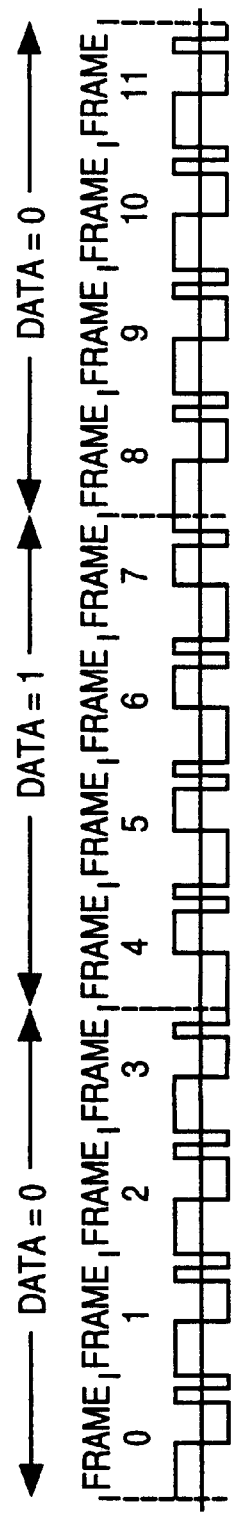
FIG. 9A (BASEBAND PN SIGNAL, FRAME LENGTH = 7, DATA PERIOD = 4 FRAMES)
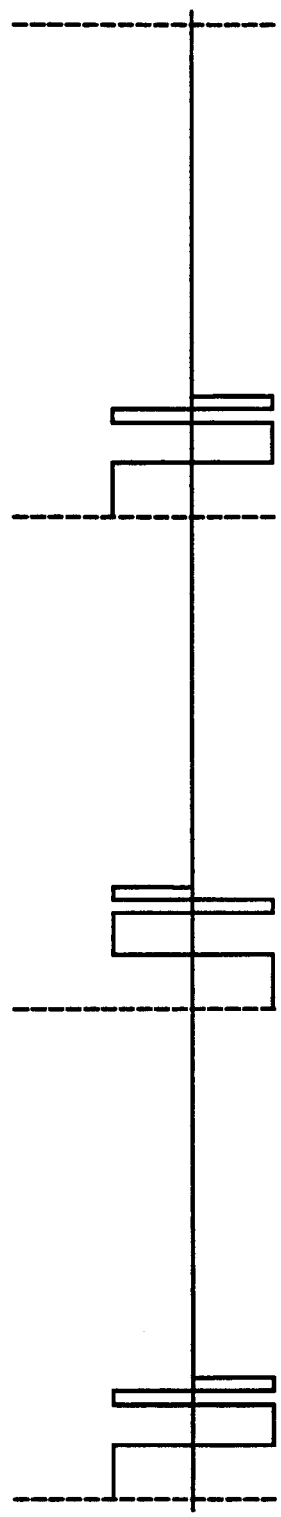
FIG. 9B (OUTPUT AFTER SUMMING GROUPS OF 4 PN FRAMES)

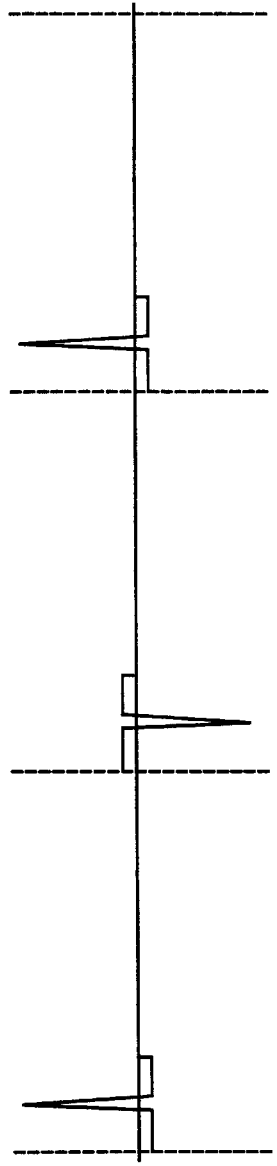
FIG. 9C (OUTPUT AFTER FFT BASED MATCHED FILTER)
FIG. 9D (OUTPUT AFTER SQUARING MATCHED FILTER OUTPUTS)
FIG. 9E (OUTPUT AFTER SUMMING OUTPUTS OF D)

GPS RECEIVERS AND GARMENTS CONTAINING GPS RECEIVERS AND METHODS FOR USING THESE GPS RECEIVERS

RELATED APPLICATIONS

This application is a divisional application of U.S. patent application Ser. No. 08/723,220, filed Oct. 7, 1996, now U.S. Pat. No. 5,825,327, which is a continuation in part of a patent application filed on Mar. 8, 1996 by Norman F. Krasner entitled "An Improved GPS Receiver and Method For Processing GPS Signals" (Ser. No. 08/612,669), now U.S. Pat. No. 5,663,734, and is also a continuation in part of a patent application filed on May 23, 1996 by Norman F. Krasner entitled "Combined GPS Positioning System and Communications System Utilizing Shared Circuitry" (Ser. No. 08/652,833), now U.S. Pat. No. 6,002,363.

This application is also related to and hereby claims the benefit of the filing date of a provisional patent application by the same inventor, Norman F. Krasner, which application is entitled Low Power, Sensitive Pseudorange Measurement Apparatus and Method for Global Positioning Satellites Systems, Ser. No. 60/005,318, filed Oct. 9, 1995.

FIELD OF THE INVENTION

The present invention relates to GPS receivers and methods of tracking objects using GPS receivers and to garments containing GPS receivers.

BACKGROUND OF THE PRESENT INVENTION

GPS receivers with multiple GPS antennas are known in the prior art. Examples of such systems are described in U.S. Pat. Nos. 5,341,301; 5,185,610; and 5,177,493. In these systems, dedicated serial correlating hardware is coupled to each GPS antenna That is, for each GPS antenna, there is corresponding serial correlator hardware. Thus, when a GPS receiver includes several GPS antennas, there will be considerable additional hardware required for each GPS antenna. This additional hardware adds to the cost and weight of such a system. Therefore, such systems are not favored despite the fact that multiple GPS antennas tend to improve the performance of GPS receivers due to the problems from partial or complete blockage of GPS signals which plague GPS receivers.

GPS antennas, because of the blockage problem, tend to be mounted in such a way that they protrude from the device or object which carries the receiver. In this way, the antenna can have an unobstructed view of the sky and any GPS satellites in view at any particular time. Consequently, it is possible to place a GPS receiver in a backpack and mount the antenna as a rigid post on the back of the backpack to provide an unobstructed view of the sky. However, no GPS receivers have been placed in garments along with the GPS antenna, such as the flexible strip antenna on the garment.

The combination of GPS systems and other communications is receiving considerable interest, especially in the areas of personal and property tracking. An example of such a combination is shown in U.S. Pat. No. 5,225,842. The communication link allows a GPS receiver located on a mobile person or object to transmit its accurately determined position to remote locations which monitor this activity. Applications of the technology include security, truck fleet tracking, emergency response, inventory control, etc. The prior art has performed such combinations by mating separate GPS receivers and communication systems using suitable electronic interfaces between the two, for example, serial communication ports, etc. Moreover, these systems use conventional serial correlating approaches to acquiring and tracking GPS satellite signals.

SUMMARY OF THE INVENTION

The present invention provides a GPS receiver having multiple GPS antennas which are coupled to one digital memory or several digital memories in order to store digitized signals which are obtained through the multiple GPS antennas. A digital processor is coupled to the digital memory or memories in order to process the digitized signals. When an embodiment of the present invention includes two GPS antennas which provide first and second digitized signals, the digital processor will typically process the first digitized signals to provide a first position information, such as a pseudorange, and process the second digitized signals to provide a second position information. Then, the processor will typically determine which position information has the lower error and select that position information as the proper position information which indicated the position of the GPS receiver.

In a typical embodiment of the present invention, the digital processor will process the first and second digitized signals by performing fast convolution operations. In one embodiment, the digital processor will perform a preprocessing operation on the first digitized signals to provide first results for the first digitized signals and perform a fast convolution operation on the first results to provide second results for the digitized signals and then perform a post processing operation on the second results to provide a third result for the first digitized signals which may then be used to provide a pseudorange from the first digitized signals. Similarly, these operations are also performed on the second digitized signals and a comparison is made between the results obtained from the first digitized signals and the second digitized signals in order to select the position information having the lower error.

In one embodiment of the present invention, selected position information is then transmitted through a transmitter which is typically coupled to the digital processor and a communication antenna. This transmitted position information is received at a base station which may then be used to track the GPS receiver. As described in more detail below, the collection of the GPS signals through the multiple GPS antennas may occur sequentially in time or concurrently in time depending on the architecture of the GPS receiver. The collection concurrently of GPS signals through multiple GPS antennas will typically require several digital memories each concurrently receiving digitized signals from its corresponding GPS antenna.

The present invention also provides a garment, such as a jacket or pants, which includes a GPS antenna and a GPS receiver along with a communication antenna and a communication transmitter. In one embodiment a first GPS antenna is attached to the garment, and a GPS receiver may also be attached to the garment and is coupled to the first GPS antenna A communication antenna may also be attached to the garment and a communication transmitter is coupled to the communication antenna and to the GPS receiver. In one embodiment of the garment of the present invention, a second GPS antenna is also attached to the garment and is also coupled to the GPS processor. In one embodiment, both the first GPS antenna and the second GPS antenna are flexible strip antennas which are substantially coplanar with the surface of the garment. The first and second GPS antennas may be attached to the garment by sewing the antennas to the garment. Often, the GPS antennas will be concealed in the garment or at least not readily apparent upon viewing the garment. The GPS receiver and communication transmitter need not be attached to the garment For example, either the GPS receiver or the communication transmitter (or both) may be attached to a belt which is near the garment, and the GPS receiver and/or communication transmitter is coupled to its corresponding antenna through a flexible conductor.

In a typical embodiment, the GPS receiver in the garment will include a digital memory which is coupled to the GPS antenna to receiver digitized signals obtained through the GPS antenna and will further include a digital processor coupled to the digital memory to process the digitized signals, usually by performing fast convolutions, to provide position informations. The position information may be a pseudorange which is then transmitted by the communication transmitter through the communication antenna In a typical embodiment, the garment may also include a communication receiver which is coupled to the GPS receiver. This communication receiver may receive satellite data information, such as satellite Doppler information and may receive GPS positioning commands which cause the GPS receiver to determine the position of the receiver or to determine a pseudorange. The communication receiver need not be attached to the garment; for example, this receiver may be attached to a belt which is near the garment, and this receiver is coupled to an antenna which may be on the receiver or on the garment.

A method of tracking an object is also described as another aspect of the present invention. This method includes obtaining at the object a positioning command, and as a result receiving first GPS signals through a first GPS antenna on the object. First digitized samples of the first GPS signals are stored in a digital memory at the object and a processor at the object processes digitally the first digitized samples by performing a plurality of fast convolutions on the samples. Then, a position information, such as a pseudorange, is transmitted from the object.

In one embodiment of this method of tracking, multiple GPS antennas may be utilized, or the object which is tracked may be wearing the garment of the present invention.

In an embodiment of the method of tracking of the present invention, the positioning command may be received at the object by generating the command at the object without any transmission of the command from a station remote from the object. This may be done so that a user of the object may activate the position determination and transmission sequence upon the occurrence of a panic condition or a medical emergency or other medical condition. Alternatively, the positioning command may be transmitted from a station which is remote to the object in order to track the object at the request of the operator of the station which is remote from the object.

BRIEF DESCRIPTION OF THE DRAWINGS

The present invention is illustrated by way of example and not by way of limitation in the figures of the accompanying drawings in which reference numerals indicate similar elements.

FIGS. 9A, 9B, 9C, 9D, and 9E illustrate the signal processing wave forms at various stages of processing of GPS signals according to the methods of one embodiment of the present invention.

DETAILED DESCRIPTION OF THE PREFERRED EMBODIMENT

Figure 1A:
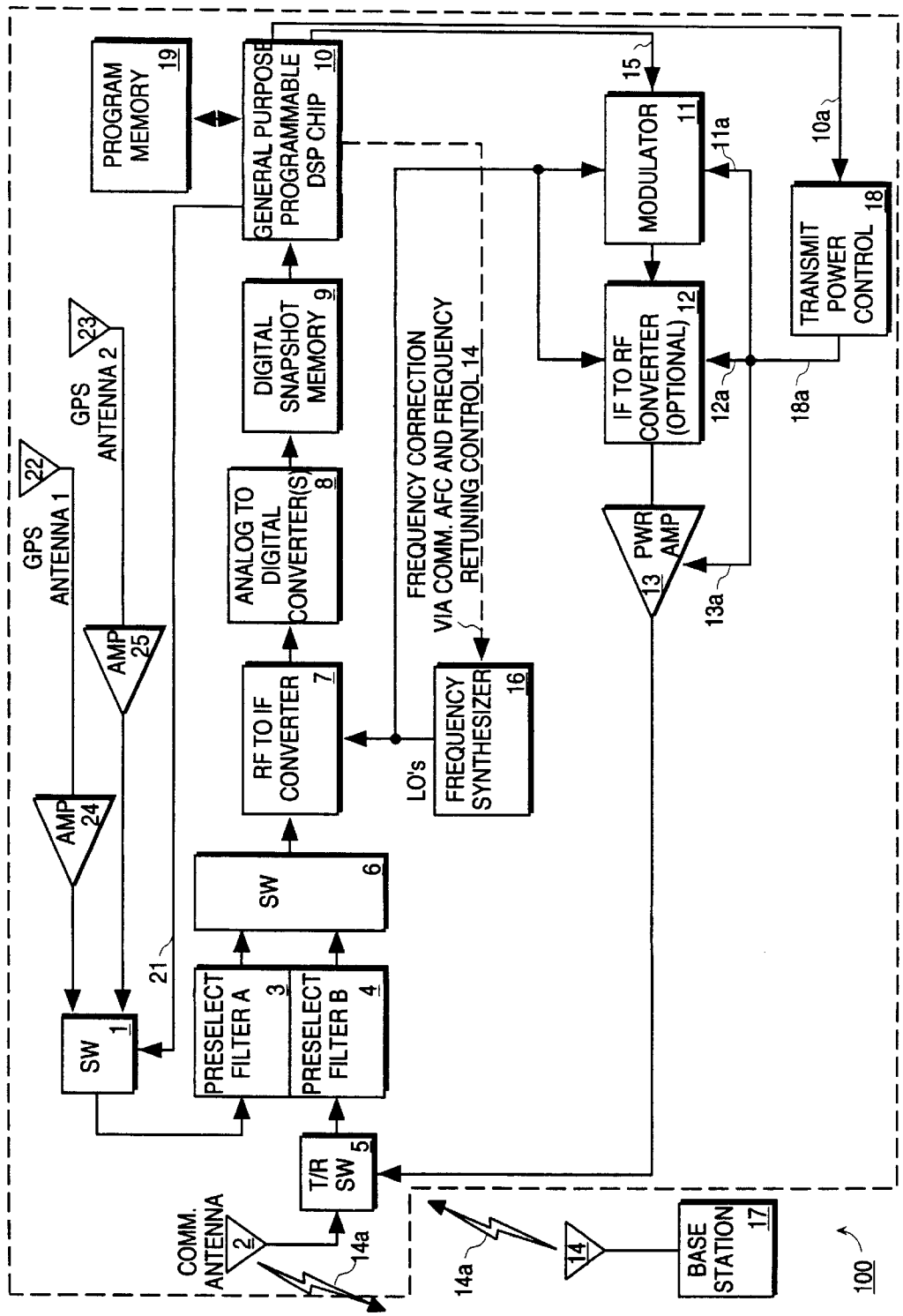
FIG. 1A is a block diagram of major components of a mobile combined system having a combined GPS reception system as well as a communication system which can establish a communication with a base station.
Figure 6A:
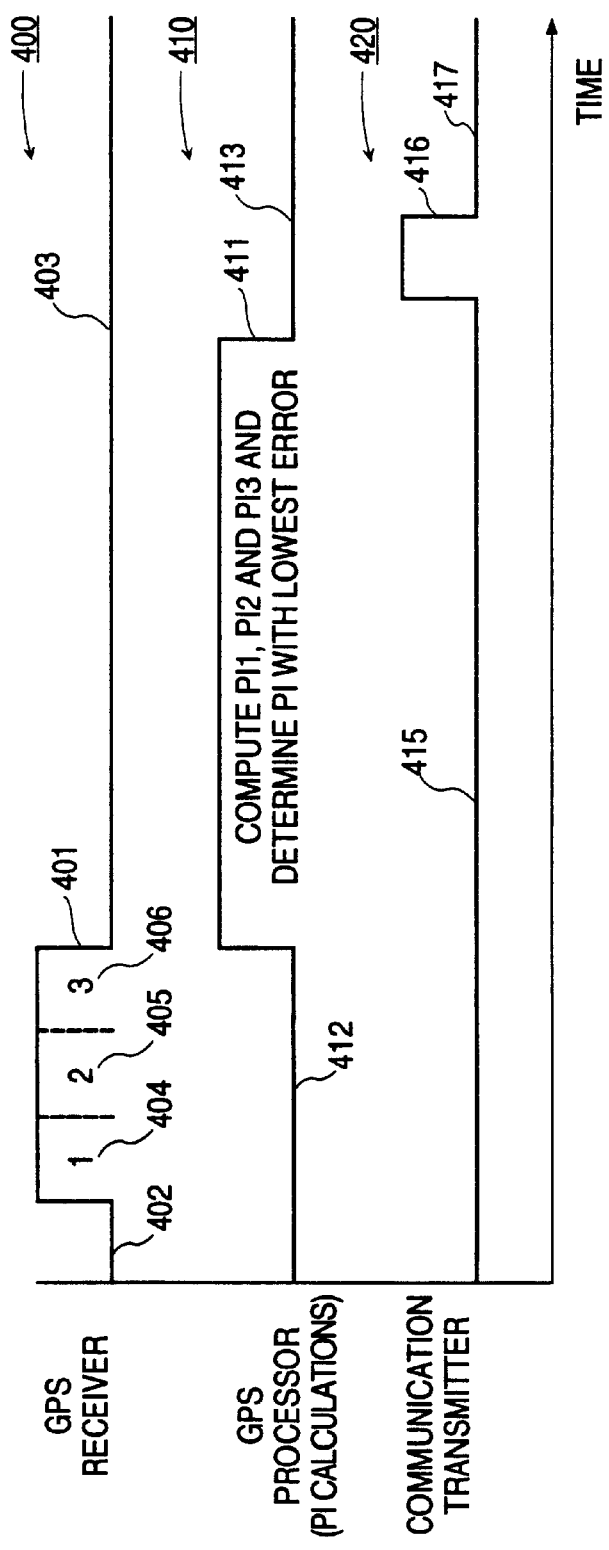
FIGS. 6A, 6B, and 6C illustrate three embodiments of the present invention which utilize multiple GPS antennas.
Figure 6B:
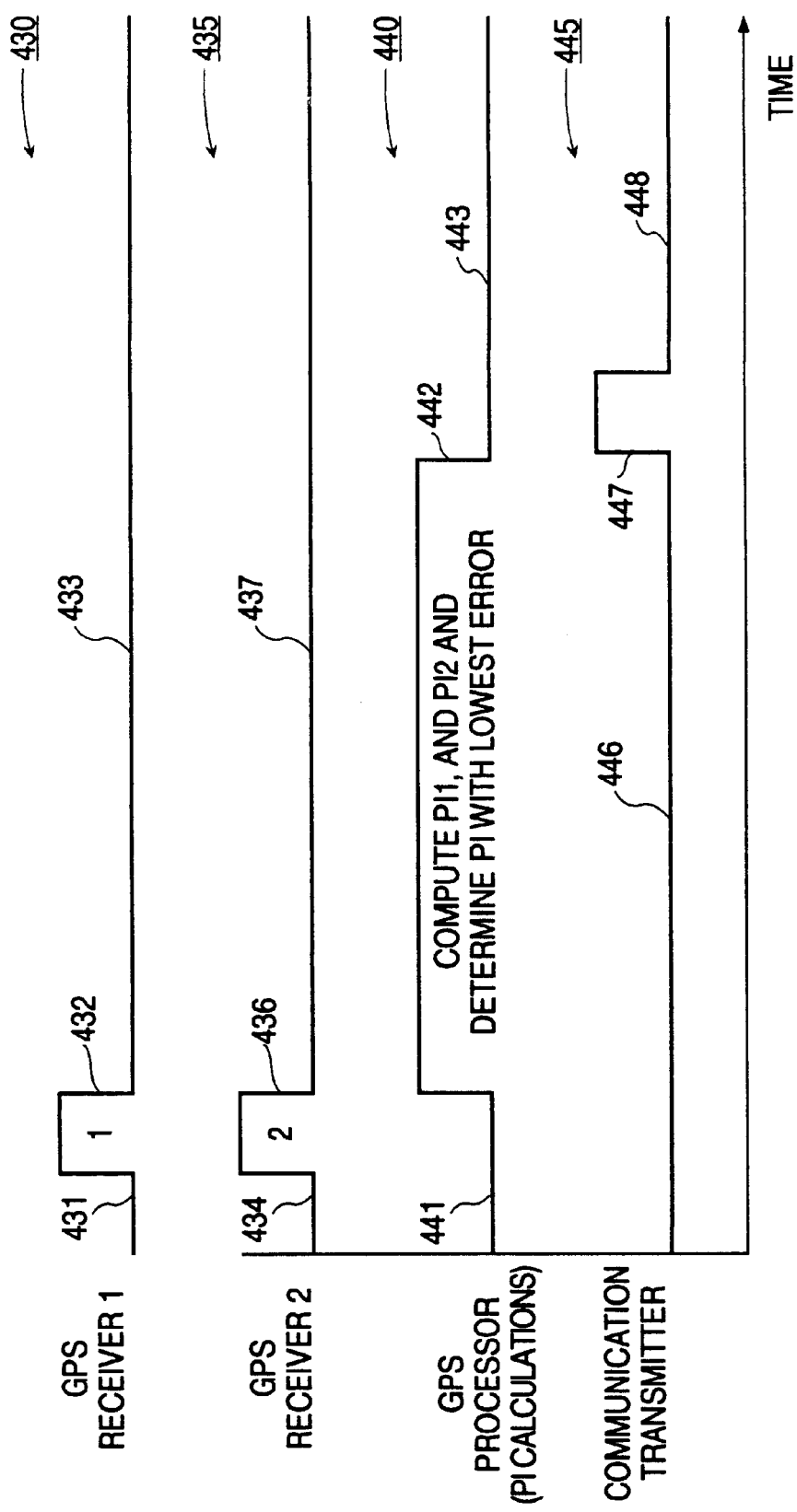
Figure 6C:
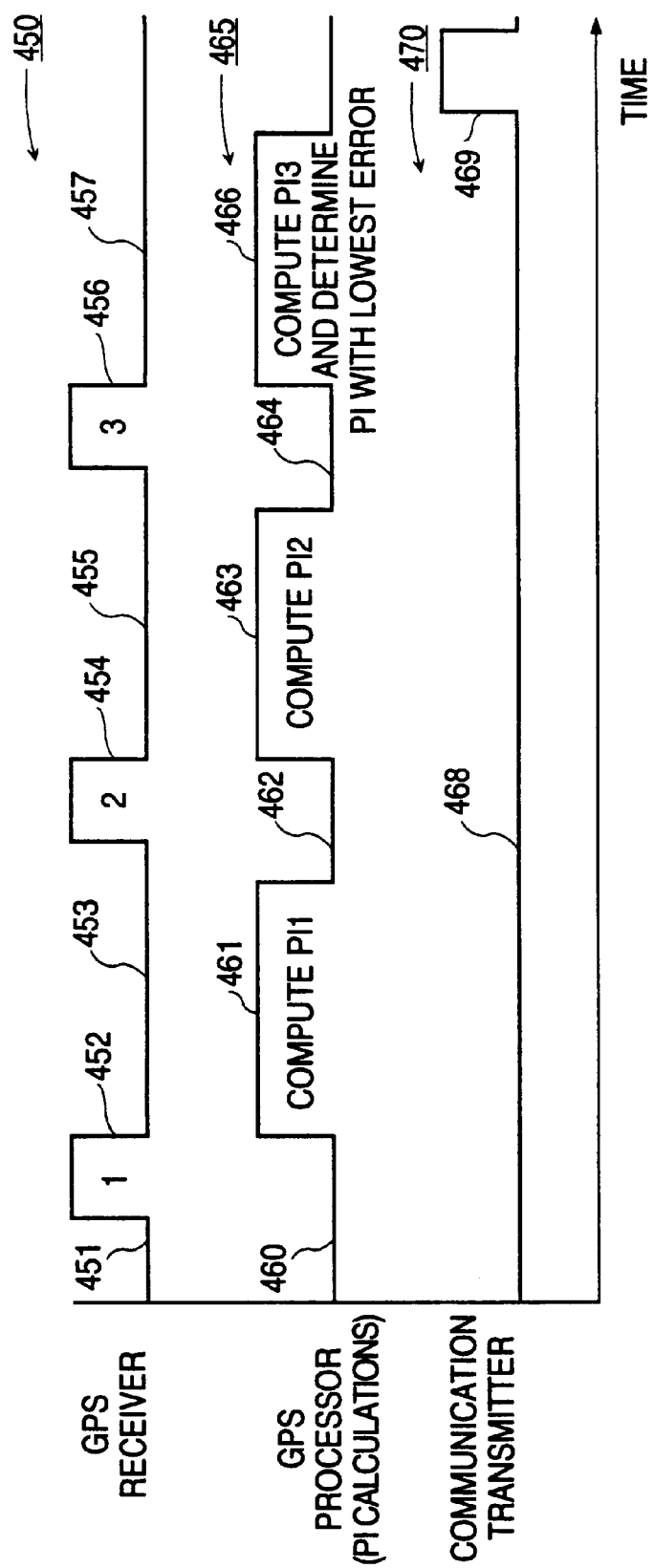

An example of a GPS receiver of the present invention which has multiple GPS antennas is shown in FIG. 1A. This figure also shows an example of a combined GPS receiver and communication system having shared circuitry. The unit 100 includes circuitry for performing the functions required for processing GPS signals as well as the functions required for processing communication signals received through a communication link. The communication link, such as communication link 14A, is typically a radio frequency communication link to another remote component, such as the base station 17 having a communication antenna 14. The unit 100 includes two GPS antennas 22 and 23 which are coupled through switch 1 to a preselect filter A as shown FIG. 1A. Signals received through GPS antenna 22 are amplified by the low noise amplifier 24 and these amplified signals are provided to the switch 1 as one of two inputs to switch 1. Signals received through GPS antenna 23 are amplified by the low noise amplifier 25, which then provides the amplified signals to the switch 1 as the other of two inputs to switch 1. The output of switch 1 is provided to preselect filter 3 which removes interference outside of a particular signal band which in this case corresponds to that of GPS signals. The switch 1 has a control input 21 which receives a control signal from the digital processing chip 10 which in one embodiment may be a general purpose programmable digital signal processing chip. In an alternative embodiment, the digital processor 10 may be a special purpose, custom GPS chip or plurality of chips designed for the purpose of implementing the present invention. The switch input 21 receives the control signals from the digital processor 10 and these control signals select one of the two inputs to be then outputted from the switch 1. The switching of switch 1 between the GPS signals from the two GPS antennas may be performed in numerous ways: for example, as shown in FIG. 6A, GPS signals from multiple GPS antennas may be sequentially collected and stored and then the computations from the stored signals are performed by the digital processor. Alternatively, the collection of first GPS signals from a first GPS antenna may occur along with the computation of a first position information from the first GPS signals before the collection of second GPS signals from a second GPS antenna, this is shown in FIG. 6c.

In one embodiment of the present invention, the switch 1 in unit 100 is controlled to provide a portion of time (for example 0.25 seconds) of GPS signals from GPS antenna 22, and then the switch 1 is switched under control of a control signal from the digital processor 10 to provide at the output of switch I GPS signals from a GPS antenna 23 for a portion of time (for example 0.25 seconds). In this manner, signals from GPS antenna 22 are sent through switch 1 and through filter 3 and through switch 6, converted in converter 7 and digitized in converter 8 and then stored in memory 9 for later processing. Then, GPS signals from GPS antenna 23 are switched through switch 1, and filter 3 and switch 6 and then converted by converters 7 and 8 and stored as digitized samples in the memory 9 along with the samples of digitized signals representing the first GPS signals obtained through the GPS antenna 22.

Figure 1B:
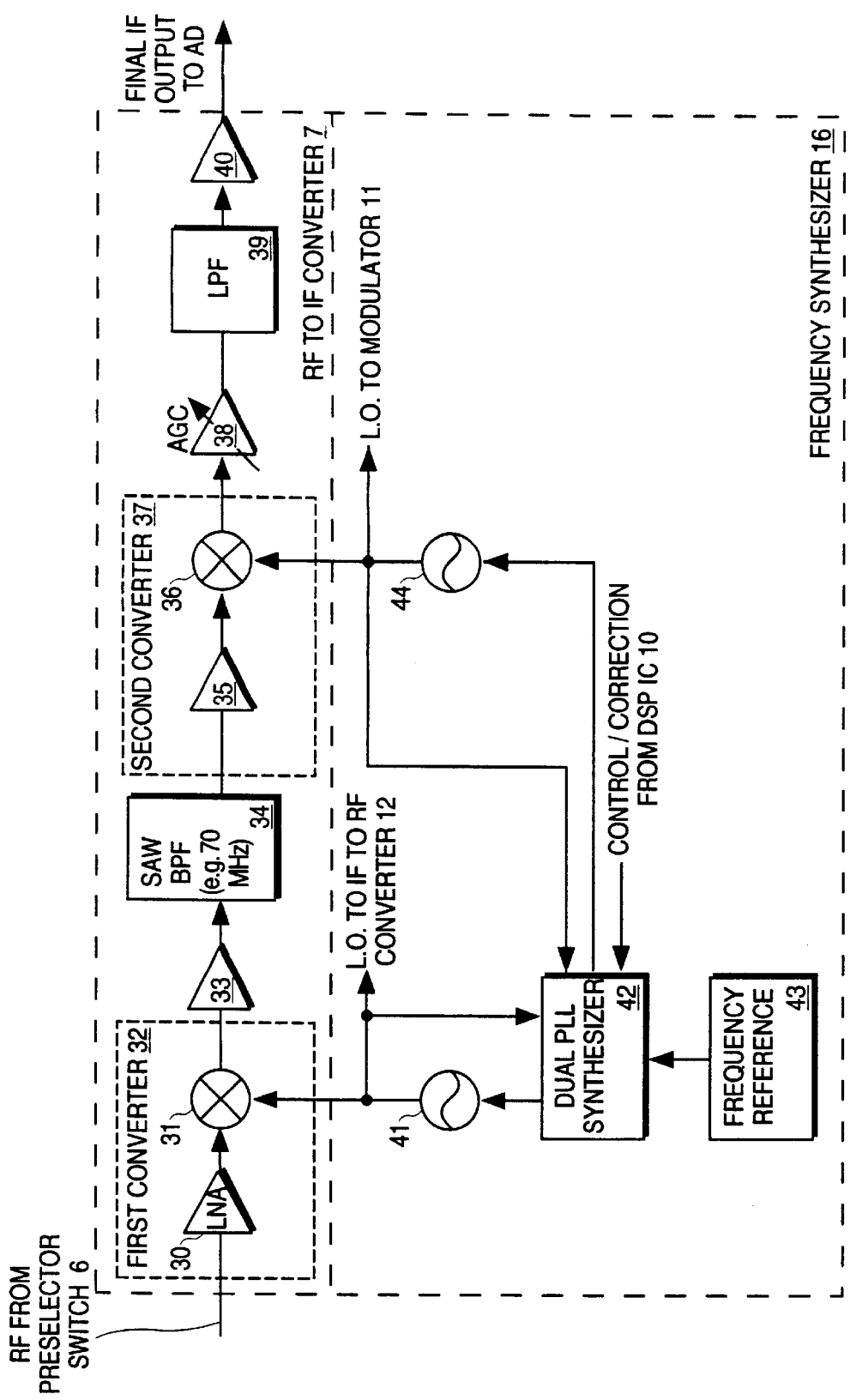
FIG. 1B shows a block diagram of a typical implementation for the RF to IF converter and frequency synthesizer of FIG. 1A.

It will be appreciated that the switch 6 selects the signal from the preselect filter 3 for input to the RF to IF converter 7 when the GPS signals are being collected in accordance with the present invention. When the communication signals from the communication link 14A are being collected through communication antenna 2 for demodulation, the switch 6 selects the signal from the preselect filter 4 for input to the converter 7. The output of the switch 6 is coupled to the input of the radio frequency (RF) to intermediate frequency (IF) converter 7. This converter 7 translates the GPS or communication signal to a suitable intermediate frequency, for example 70 MHz. It then provides a further translation to a lower intermediate frequency, for example 1 MHz. Each converter within the RF to IF converter 7 typically consists of an amplifier and a mixer, as shown in FIG. 1B. The components of the first converter are normally sufficiently wideband to encompass a wide frequency range (for example 800 to 2000 MHz) and for most cases are sufficiently broadband to handle the frequency ranges spanned by the GPS signals and the most important communication signals.

The output of the RF to IF converter 7 is coupled to the input of an analog to digital (AID) converter 8 which digitizes the output signals from the RF to IF converter 7. In some implementations, the RF to IF converter 7 provides a pair of outputs that are in phase quadrature: in such cases, two AID converters may be employed. The output from the A/D converter 8 is coupled to an input of the digital memory 9 which can store the record of data to be processed. In some cases this memory 9 may be bypassed and the data sent directly to the processor component 10 (which may be a DSP chip as shown or a set of digital processing chips) if the data rate output from the A/D 8 is sufficiently low. The digital memory 9 is typically used in processing the GPS signals which are typically stored in the memory 9. The digital memory 9 is also normally employed for communication signals that are packetized—that is, signals consisting of bursts of data bits followed by long periods of inactivity. This is the primary form of communication signaling envisioned to be used with the present invention. However, continuous signaling, such as many cellular type signals, may be processed in a continuous manner by the digital processor 10.

The digital memory 9 is coupled to the digital processor 10 in a typical embodiment in order for the processor to read data from the digital memory 9. In other embodiments, the processor may be able to write to the memory 9 as well as read from it This would permit storage of intermediate computational results. In another embodiment, the memory 9 may be conventional dual port memory, having one input port coupled to receive output from the A/D converter 8 and another input port coupled to receive data from processor 10.

It will be appreciated that the processing component 10 receives communication signals sent through the communication link 14A by converting the communication signals in converter 7 and digitizing those signals through converter 8 and storing those signals in memory 9 or processing them directly. In this fashion, the processor 10 demodulates the communication signal in order to determine the commands in the communication signal or other data (e.g. Doppler data or data representative of ephemeris of satellites in view) in the communication signal.

When a transmission is required through the communication link, the processor 10 generates the data to be transmitted and baseband digital samples of the signal. It then uses this data to modulate a carrier signal using a modulator circuit 11. Such modulation is often a digital type, such as a frequency shift keying or phase shift keying. Analog modulation, such as frequency modulation, may also be used. The carrier frequency at which the modulation is performed may or may not be at the final RF frequency of the communication signal. If it is at an intermediate frequency (IF) then an additional IF to RF converter 12 is employed to translate the signal to a final RF frequency for the communication signal. A power amplifier 13 boosts the signal level, and this boosted signal is then fed to the communication antenna 2 through a transmit/receive (T/R) switch 5 whose purpose is to isolate the sensitive receiver stage from the strong signal levels output from the power amplifier 13. In this manner, a communication signal containing data representative of position information (e.g. pseudoranges to various satellites or a latitude and longitude of the unit 100 ) is transmitted to a base station, such as base station 17 through communication link 14A.

It may be appreciated that, at least in one embodiment, the same frequency synthesizer is used to produce the local oscillators for all operational modes. Those modes include the reception of data representative of GPS signals, the reception of communication signals from the communication link 14A and the transmission of communication signals to the communication link 14A. It should also be noted that the RF to IF converter 7, the analog to digital converter 8, the digital memory 9, and the digital processor 10 are common to all operational modes in at least one embodiment of the present invention. Of course, other peripheral circuitry such as power supplies would normally be common to all such modes.

It will also be appreciated that, according to one embodiment of the present invention, a power management circuit may be implemented using power management algorithms stored in memory 19. These algorithms control the digital processor 10 which in turn controls the transmit power control 18. The transmit power control 18 provides a controlled power signal for the power amplifier 13, the converter 12, and the modulator 11 such that after transmission of a communication signal, the transmit power control unit 18 may cause modulator 11, converter 12 and amplifier 13 to enter a reduced power state. These components typically remain in this reduced power state until a further transmission through the communication link 14A is required. A typical example of this embodiment is a two-way pager system where the mobile unit 100 performs the functions of a two-way receiver and transmitter (in a two way pager system), and the transmitter is turned off (or otherwise consumes reduced power) when the transmitter is not transmitting. Furthermore, power consumption may be further reduced by controlling the amplifiers 24 and 25 such that these amplifiers are only in a full power state when the switch 1 has been selected to receive GPS signals through the corresponding GPS antenna. For example, while receiving GPS signals through GPS antenna 22 the amplifier 24 may receive full power while amplifier 25 is kept in a reduced power state. When the switch 1 selects GPS signals received through GPS antenna 23, the amplifier 25 is returned to full power state and the amplifier 24 is placed in a reduced power consumption state under control of power management circuit which is similar to the transmit power control 18.

FIG. 1B provides some additional details of the RF to IF converter 7 and its relationship to the frequency synthesizer 16, both of which are shown in FIG. 1B. A dual frequency synthesizer 42 as shown in FIG. 1B is commonly available and is used to provide tunable local oscillators (L.O's). These may be tuned to accommodate the different RF's frequencies for the different operational modes. The amplifier 30 in the first converter 32 receives the output from the switch 6 and amplifies that output to provide an input to the mixer 31 which also receives an input from the oscillator 41. The output from the mixer 31 is provided to an input of the amplifier 33, the output of which is coupled to the input of a bandpass filter (BFP) 34. The output from this filter 34 is coupled to the input of the second converter 37 which also includes an amplifier 35 and mixer 36. The output from the mixer 36 is provided to an automatic gain control 38 which automatically controls the gain of the signal and provides an output to a low pass filter 39, the output of which is amplified by an amplifier 40 and provided as the output of the converter 7 to the input of the analog to digital converter 8. Local oscillators 41 and 44 provide the tuned frequencies for the two converters 32 and 37 in order to perform demodulation in the reception operational modes of the invention. These local oscillators 41 and 44 also provide the tuned frequencies for the modulator 1 1 and the converter 12 in the transmission mode of the present invention. It will be appreciated that the use of a general purpose digital signal processing (DSP) integrated circuit chip (or several chips in a chip set) to process common communication signals is well known to those skilled in the art. As examples of such processing, one can refer to the data sheets of the parts TMS 320C545 and TMS 320C546 from Texas Instruments of Dallas, Tex. These data sheets describe the processing of GSM signals that are utilized in the European digital cellular networks.

When receiving a communications signal (e.g. from a base station 17), the processor 10 causes the frequency synthesizer 16 to adjust its first local oscillator 41 to provide an output frequency which is a value either above or below the carrier frequency of the communication signal by an amount equal to the center frequency of the SAW filter 34.

When receiving a GPS signal (e.g. from a GPS satellite) the processor 10 causes the local oscillator 41 to provide an output frequency which is a value either above or below the carrier frequency of the GPS signal (1575.42 MHz for the U.S. GPS system) by an amount equal to the center frequency of the SAW filter 34. In most situations, the second local oscillator 44 will be tuned to the same frequency in both cases and thus the same final IF will be produced in both cases. It will be appreciated that, in a typical embodiment, the processor 10 will provide the control signals (e.g. interconnect 14 shown in FIG. 1A) to the frequencies synthesizer 16 in order to tune the oscillators (e.g. local oscillator 41) for either GPS signal reception or communication signal reception. Similarly, the processor 10 will provide the control signals to the frequency synthesizer 16 when local oscillators signals are required for transmission of communication signals through modulator 11 and, optionally, converter 12.

The sharing of common circuitry in the communication system and in the GPS receiver as described herein and as shown in FIG. 1A along with the use of multiple GPS antennas as shown in FIG. 1A provides a compact, inexpensive GPS/communication system having multiple antennas. As noted above, prior art GPS receivers with multiple GPS antennas require additional serial correlating hardware. The present invention considerably streamlines a GPS receiver system having multiple antennas as well as a communication system for receiving GPS positioning commands and data and for transmitting position information back to a base station.

Figure 1C:
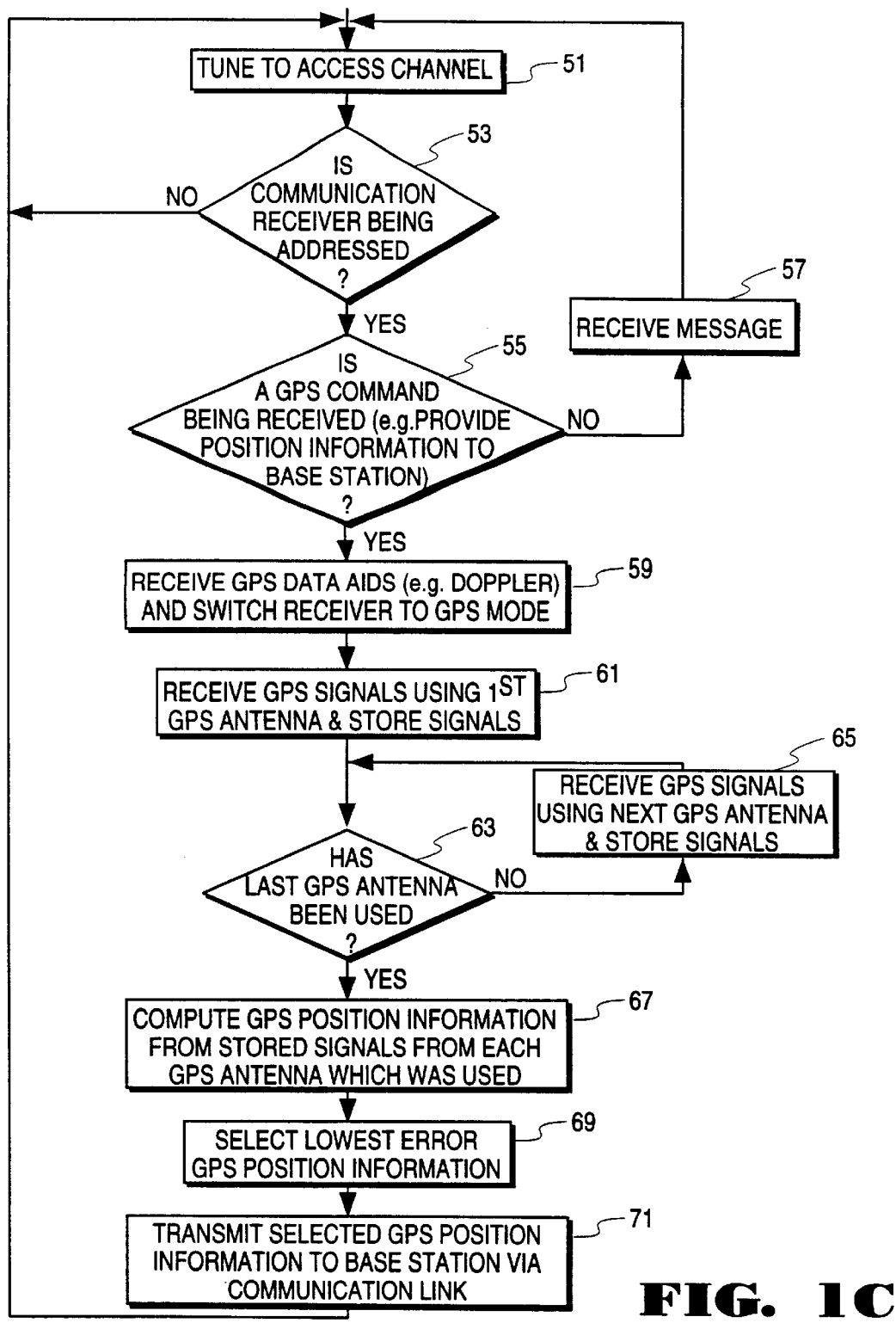
FIG. 1C illustrates a flowchart which indicates various processing steps in one embodiment of the present invention.

The flowchart of FIG. 1C shows an example of how the apparatus of FIG. 1A may be utilized in a typical operational scenario. In this situation, the receiver begins in a communications receiving mode such that the communication signals from the communication link 14A are being monitored. Therefore, in step 51, the processor 10 tunes the converter to the communication access channel. This a channel (typical of cellular networks) that broadcasts addresses of users for which there are messages and assigns such users to other channels in which they may communicate. If the receiver is being addressed as determined in step 53, then the processor 10 tunes to the specified channel and, during its acquisition, measures the carrier frequency accurately in order to calibrate the local oscillator in the unit 100. If there is a command to determine position, which may be referred to as a GPS command as indicated in step 55, then this measurement of the carrier frequency allows the GPS receiver to compensate for local oscillator errors thereby speeding the acquisition of the GPS signals. If no GPS command is being received as determined in step 55, the communication receiver in step 57 receives the communication message which is processed by the processor 10 and then returns to step 51 in order to continue to monitor the communication channel. The processor 10 will continue to monitor the communication channel as shown in steps 51 and 53 until a GPS command is received as determined in step 55. Upon receiving a GPS command as determined in step 55, the unit 100 enters GPS mode as shown in step 59, although before entering into GPS mode, the processor 10 may receive GPS data 8, such as Doppler information and/or other information using the communication link 14A. Then, the processor causes the system to enter GPS mode by retuning the receiver to the GPS band. Then in step 61, the processor causes the system 100 to receive first GPS signals using the first GPS antenna and stores those signals in the digital memory 9. In step 63, the processor determines whether the last GPS antenna has been used since receiving the last GPS command. If not, the processor causes in step 65 the GPS receiver to receive GPS signals using the next GPS antenna and stores digitized samples of those signals in the digital memory 9. The processor continues in step 63 and 65 to collect GPS signals through different GPS antennas until the last GPS antenna (which is desired to be used) has been used. This allows multiple GPS antennas to be used to collect multiple GPS signals through the different GPS antennas. Typically, these signals will be stored in a digital memory 9 and then processed later although various alternatives may be employed as described herein.

Step 67, the processor 10 computes the GPS position information from stored signals from each GPS antenna which was used during the collection process associated with steps 61, 63 and 65. This position information is typically calculated in the manner described herein using fast convolutions with preprocessing and post-processing operations in order to provide increased sensitivity which cannot be provided by standard GPS receivers.

In step 69, the processor then selects the best position information by typically determining the GPS position information (e.g. for a particular satellite) calculated in step 67 which has the lowest error associated with that position information. For those digitized samples collected through a GPS antenna for which no position information could be obtained due to poor reception through that antenna, such position information will be treated as having the highest possible error. Such situation may be considered one in which no "fix" was obtained of the GPS signals. For those GPS signals obtained through different GPS antennas and for which fixes were obtained, the processor in effect picks the best fix by selecting the position information having the lowest error associated therewith. This is performed in one of several ways which are described below in conjunction with FIG. 8.

After selecting the GPS position information which has the lowest error, the processor in step 71 transmits the selected GPS position information back to a base station via the communication link 14A in order to permit the communication link to complete the GPS position calculation or in order to provide the position (e.g. latitude and longitude) to the base station for further tracking or other use. Depending upon the communication system and the time to perform the GPS position calculations, the same or different communication channel may be utilized as was employed during a reception of a message from the communication link 41A. If a different channel is employed, then the channel access procedure used during reception may be again utilized It will be appreciated by those in the art that the foregoing description is a typical flow according to one operational scenario. Other variations on this scenario may be practiced according to the invention. For example, a multiplicity of GPS measurements can be made through multiple GPS antennas between receptions or transmissions over the communication link. Alternatively, a large number of communication messages may be passed back and forth over the communication link, with only occasional times allocated for processing of GPS signals through multiple GPS antennas.

It will be appreciated from the following description that the system 100 shown in FIG. 1A may implement a GPS receiver having multiple GPS antennas by alternative architectures while at the same time maintaining the shared and common circuitry between the GPS system and the communication system. For example, switch 6, instead of having two inputs may have 3 inputs two of which receive GPS signals from two different GPS antennas. In this manner, the switch 6 would select between the two GPS antennas in the same manner as switch 1 and switch 6 would also switch to select communication signals through the filter 4. In this instance, two preselect filter A's may be utilized to separately filter the two different GPS signals received through the two different GPS antennas. In another alternative embodiment of the system shown in FIG. 1A, each GPS signal through its corresponding GPS antenna may be converted in a dedicated RF to IF converter. Thus at least two RF to IF converters will be present in such a system, and the selection and switching between the converters will be similar to the system shown in FIG. 3. Other variations of the system shown in FIG. 1A will be appreciated by those skilled in the art upon reference to this disclosure, including FIGS. 2A and 3 herein.

Figure 2A:
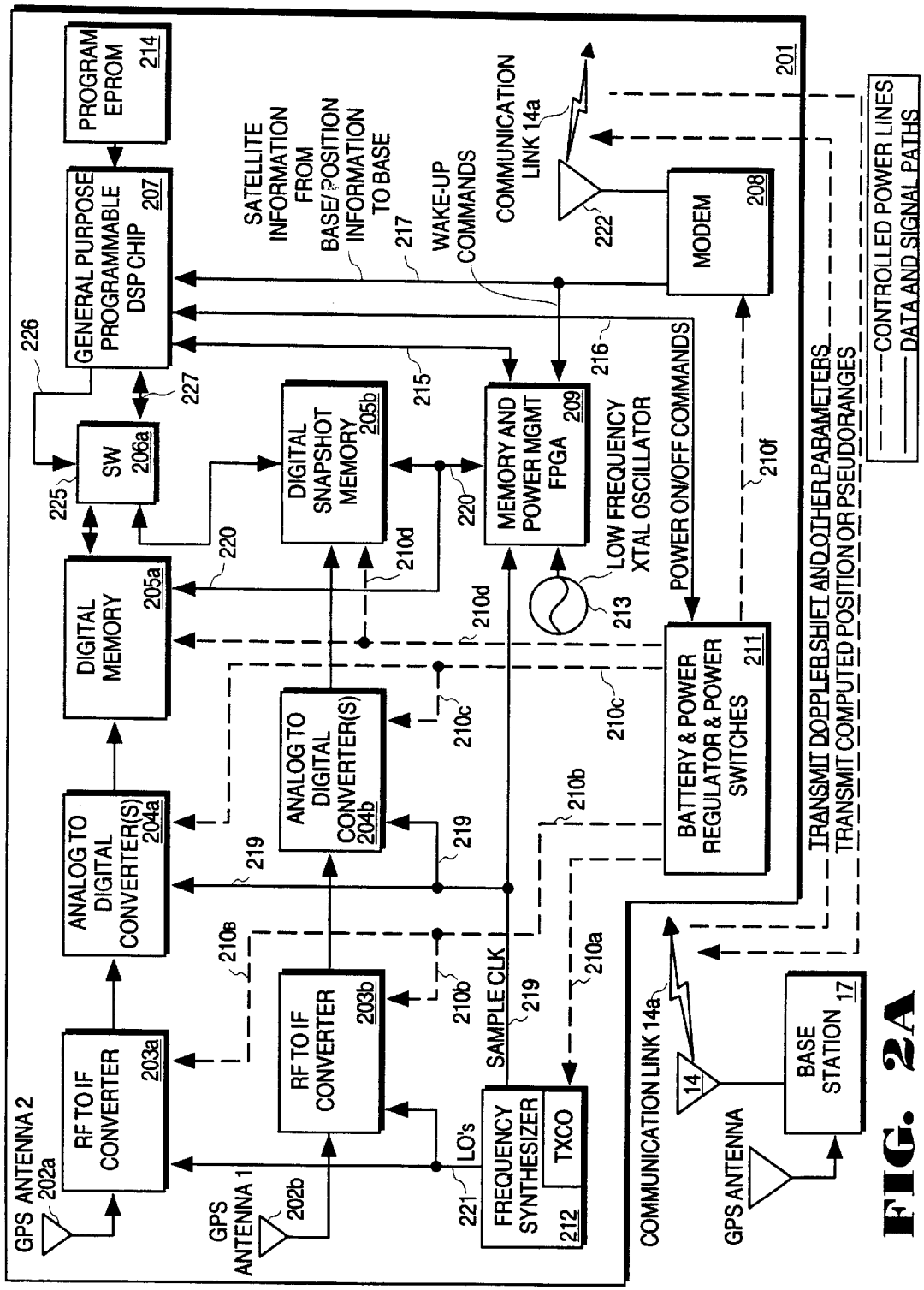
FIG. 2A is a block diagram of major components of a mobile GPS receiver and communications system.

FIG. 2A shows an alternative embodiment of a GPS receiver of the present invention having multiple GPS antennas. This GPS receiver does not employ shared, common circuitry between the GPS receiver system and the communication system because the modem 208 provides separate transmission and reception capabilities (for the communication link) while the processor 207 provides the GPS processing capabilities. The GPS receiver 201 as shown in FIG. 2A is similar to the GPS receiver shown in FIG. 1B of copending application Ser. No. 08/612,669, which was filed Mar. 8, 1996 by Norman F. Krasner, which application is hereby incorporated herein by reference. The GPS receiver 201 is similar to the receiver shown in FIG. 1B of this copending application except that each GPS antenna 202A and 202B has its own converter channel and digital memory associated therewith. In particular, the GPS antenna 202A provides GPS signals, which may be filtered, to an RF to IF converter 203A which then provides converted signals to the analog to digital converter 204A which then provides digitized samples of the GPS signals received through GPS antenna 202A to the digital memory 205A. Similarly, GPS signals received through GPS antenna 202B are provided to the RF to IF converter 203B and then to the analog to digital 204B and finally to the digital memory 205B. These converters and memories are controlled in the manner described in the copending application. This architecture as shown in FIG. 2A allows the GPS receiver to obtain concurrent GPS samples and store them concurrently in the memories. These concurrent samples are substantially simultaneous in that they are collections of GPS signals over substantially the same time period. This capability provides certain advantages over the sequential collection provided by an architecture shown in FIG. 1A and also shown in FIG. 6A. This concurrent collection of GPS signal is shown in FIG. 6B and will be described briefly below. It will be appreciated that the GPS receiver shown in FIG. 2A is not required to collect concurrent GPS samples and may collect them sequentially in a contiguous manner shown in FIG. 6a or in a non-contiguous manner shown in FIG. 6C. After collection of the digital samples in the digital memory 205A and 205B, the processor chip 207 selectively obtains the digital samples from memory 205A or 205B through the switch 206A under control of switch input 225 and the signal provided on line 226 from the processor chip 207. Data obtained on line 227 may come or go to either digital memory 205a or 205b under control of the switch 206a. The processor chip 207, which may be a general purpose programmable digital signal processing chip or a special purpose custom processing chip, will then determine position information from the two digitized sample collections stored in the two memories 205A and 205B. Thus two position information values from the two sets of digital samples will be obtained, and then the processor 207 will select the position information having the lower error associated therewith and provide that position information over bus 217 to the modem 218 which can then transmit the position information through communication antenna 222 and through communication link 14A to the base station 17.

Figure 2B:
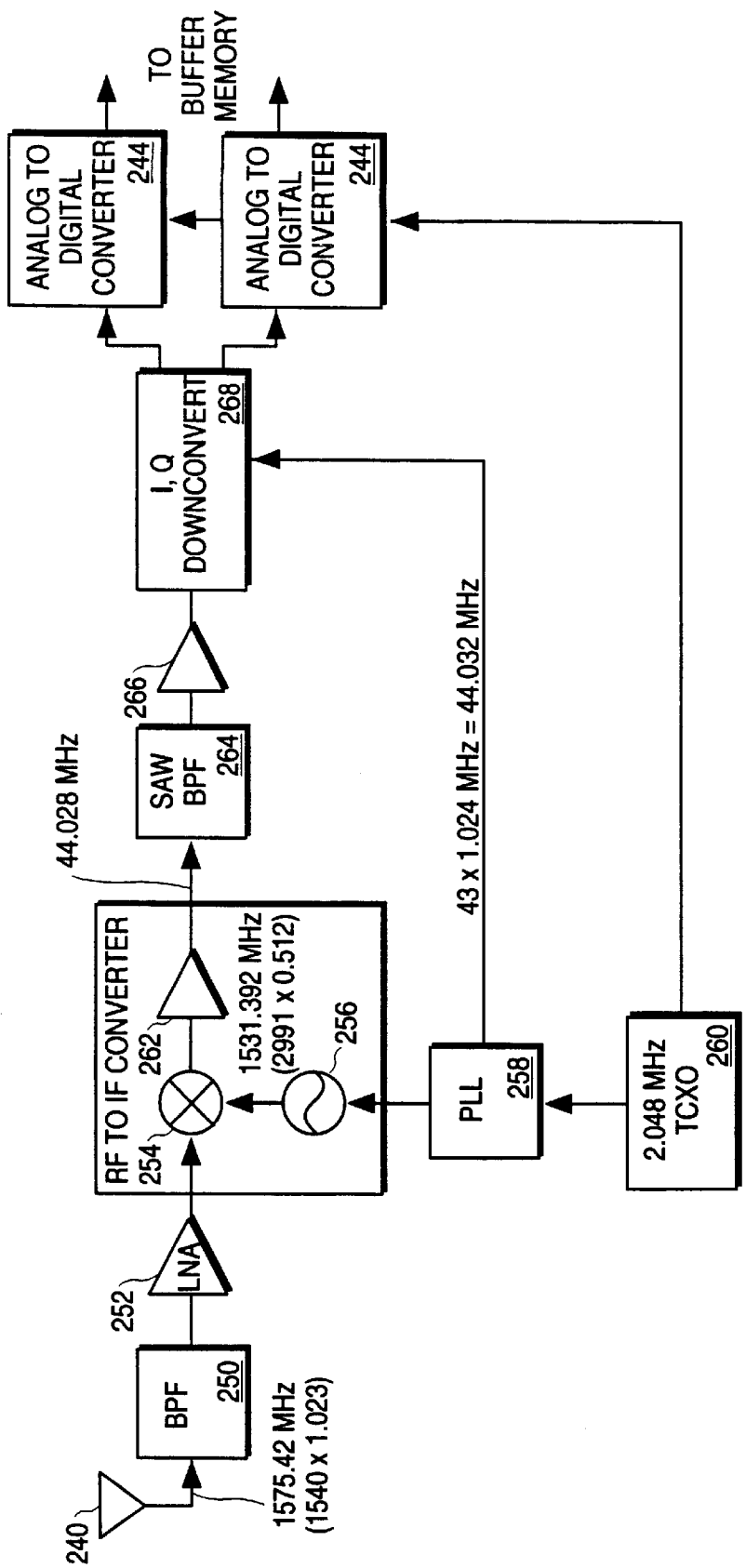
FIG. 2B shows a block diagram of a typical implementation for the RF to IF converter and analog to digital converters shown in FIG. 2A.

FIG. 2B shows in further detail one channel of the RF to IF converter and the analog to digital converters, such as the channel comprising converters 203B and 204B. The antenna 240 represents either GPS antenna 202A or GPS antenna 202b depending upon the channel. Further discussion of FIG. 2B is provided in copending application Ser. No. 08/612,669 which was filed Mar. 8, 1996 by Norman F. Krasner, which copending application is hereby incorporated herein by reference.

Figure 3:
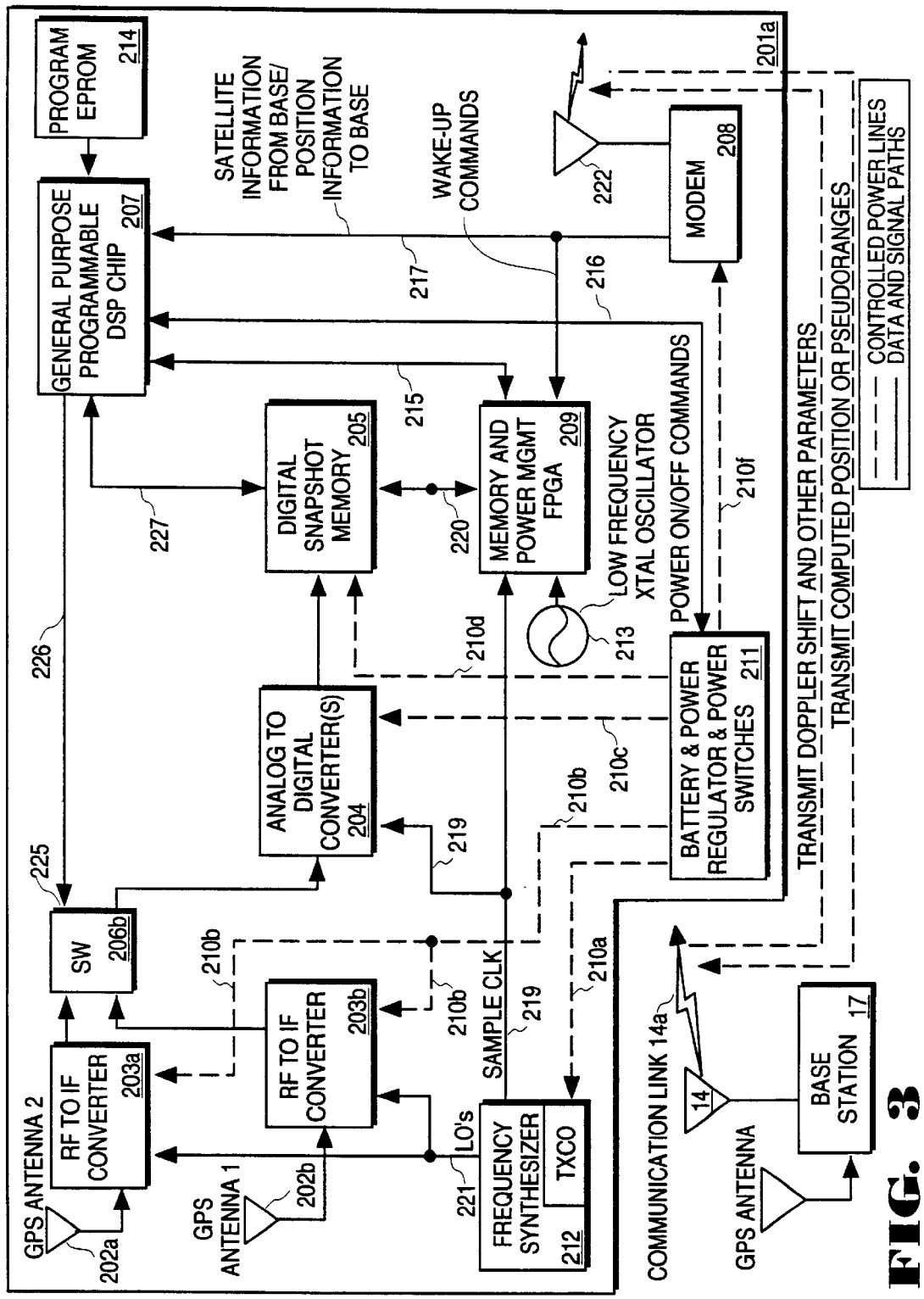
FIG. 3 shows an alternative embodiment of a GPS receiver having multiple GPS antennas according to the present invention.

FIG. 3 shows another alternative embodiment of a GPS receiver according to the present invention having multiple GPS antennas. In this embodiment, an RF to IF converter is dedicated for each GPS antenna such that the switching between GPS antennas occurs after the conversion by the respective RF to IF converter. The receiver 201A shown in FIG. 3 is similar to the receiver shown in FIG. 1b except for the variation concerning the GPS antenna and the necessary control for switching between the GPS antennas. The GPS signals received on GPS antenna 202A are provided to the RF to IF converter 203A which is then provided to the switch 206B. Similarly, the GPS antenna 202B provides GPS signals to the RF to IF converter 203B which then provides an output to an input of the switch 206B. The switch 206B is controlled by the processor 207 under control from signals provided on line 226 to the control input 225 of the switch 206B to cause the switch 206B to switch its output between the two GPS antennas as described herein. Thereafter, the analog to digital converter 204 converts the signals to digitized samples and stores those samples in the digital memory 205. The processor 207 then processes the two different digitized samples to determine two different position informations and then selects the position information having the lowest error in the manner described herein. The selected position information is then transferred over bus 217 to the modem 208 for communication through the communication antenna 222 to a base station 17.

The processing of digitized samples from multiple GPS receivers will now be described. FIGS. 6A, 6B, and 6C illustrate three alternative embodiments for processing three groups of digitized samples from three different GPS antennas. Generally, all embodiments of the present invention having multiple antennas may operate in the manner shown in FIG. 6A or FIG. 6C or a combination of these manners. The method of operation shown in FIG. 6B will typically require a GPS receiver with multiple antennas where each antenna has a portion of memory or a separate memory which is dedicated to that antenna such that signals from the antenna may be written to the memory, while signals from another antenna may be concurrently written to other memories or other portions of the same memory. FIG. 2A shows a GPS receiver having multiple antennas which can operate in the manner shown in FIG. 6B.

FIG. 6A shows a comparison of the activity over time of three components (a GPS receiver component, a GPS processor component, and a communications transmitter component) for a particular positioning operation. In particular, time line 400 shows the activity over time of the GPS receiver portion of the system, and time line 410 shows the activity of the GPS processor portion of the system, and time line 420 shows the activity of the communication transmitter portion of the system for a particular positioning operation. As shown in FIGS. 6A, the GPS receiver portion is not active in receiving GPS signals during phase 402. Upon receiving a GPS command indicating that a position determination should occur, the GPS receiver goes into the phase 401 in which it collects GPS signals from three GPS antennas in phases 404, 405 and 406 respectively. The collection and storage of these three groups of GPS signals occurs sequentially and contiguously in time during phase 401. Then, after the collection is complete, the GPS receiver enters phase 403 in which it is no longer actively acquiring and causing the storage of further GPS signals for this particular positioning operation. It will be appreciated that this is often the time, during phase 403, when power is reduced to the GPS receiver portion of the system. As shown in time line 410, the GPS processor portion relating to position information calculations is inactive as shown by phase 412 until the last group of GPS signals have been collected in phase 406. It will be appreciated that in those embodiments of the present invention in which the digital processor 10 performs both communication control and GPS control and processing, then processor 10 will actually be active during the GPS receiver phase 401. Time line 410 at phases 412 and 413 is showing that the processor 10 is not actively processing GPS signals for the purpose of performing position information calculations even though processor 10 may be active in acquiring and storing those signals. In phase 411, the processor computes three different position informations from the three different groups of GPS signals obtained through the three different GPS antennas. The processor also attempts to determine the particular position information for a particular satellite which has the lowest error. This is described in further detail in connection with step 132 of FIG. 8. After the process in phase 411 determines a position information (e.g., a pseudorange) for each satellite for which a fix was obtained, then the communication transmitter is activated in phase 416 in order to transmit the pseudo ranges calculated by the processor in phase 411 to a base station. Then the transmitter is inactivated in phase 417; this activation will typically occur by reducing power to the transmitter, which also may have reduced power during phase 415. It will be appreciated that alternative embodiments of FIG. 6A may exist, such as those where the transmitter is active during portions of phase 415 depending on the particular communication network system.

FIG. 6B shows an example where a concurrent collection of GPS signals from two different antennas is obtained during phases 432 and 436, respectively, as indicated in time lines 430 and 435. Then the GPS processor becomes activated during phase 442 in which two position informations are attempted to be calculated for each satellite in view and then the position information for that particular satellite with the lowest error is determined as described herein. Then, as shown by time line 445, the communication transmitter portion of the system is activated in phase 447 to transmit the position information as determined by the processor in phase 442.

FIG. 6C shows another embodiment of the present invention in which the collection of GPS signals by the GPS receiver portion of the system and the position information calculations are sequentially staggered over time and then the transmission of the position information for each satellite is transmitted after computing and determining the position information for a particular satellite having the lowest error.

It will be appreciated that FIGS. 6A, 6B and 6C show an example of the timing relationships between storing GPS signals and processing the signals after storage. In particular, as shown in these Figures, the processing operation begins substantially immediately after the storage process is complete. Other timing relationships may be used as will be recognized by those skilled in the art.

Once the GPS signals have been collected and stored into the digital memory (or memories) of the present invention, the processing by a digital processor of the GPS signals which are stored is performed in a manner which is now described.

Figure 8:
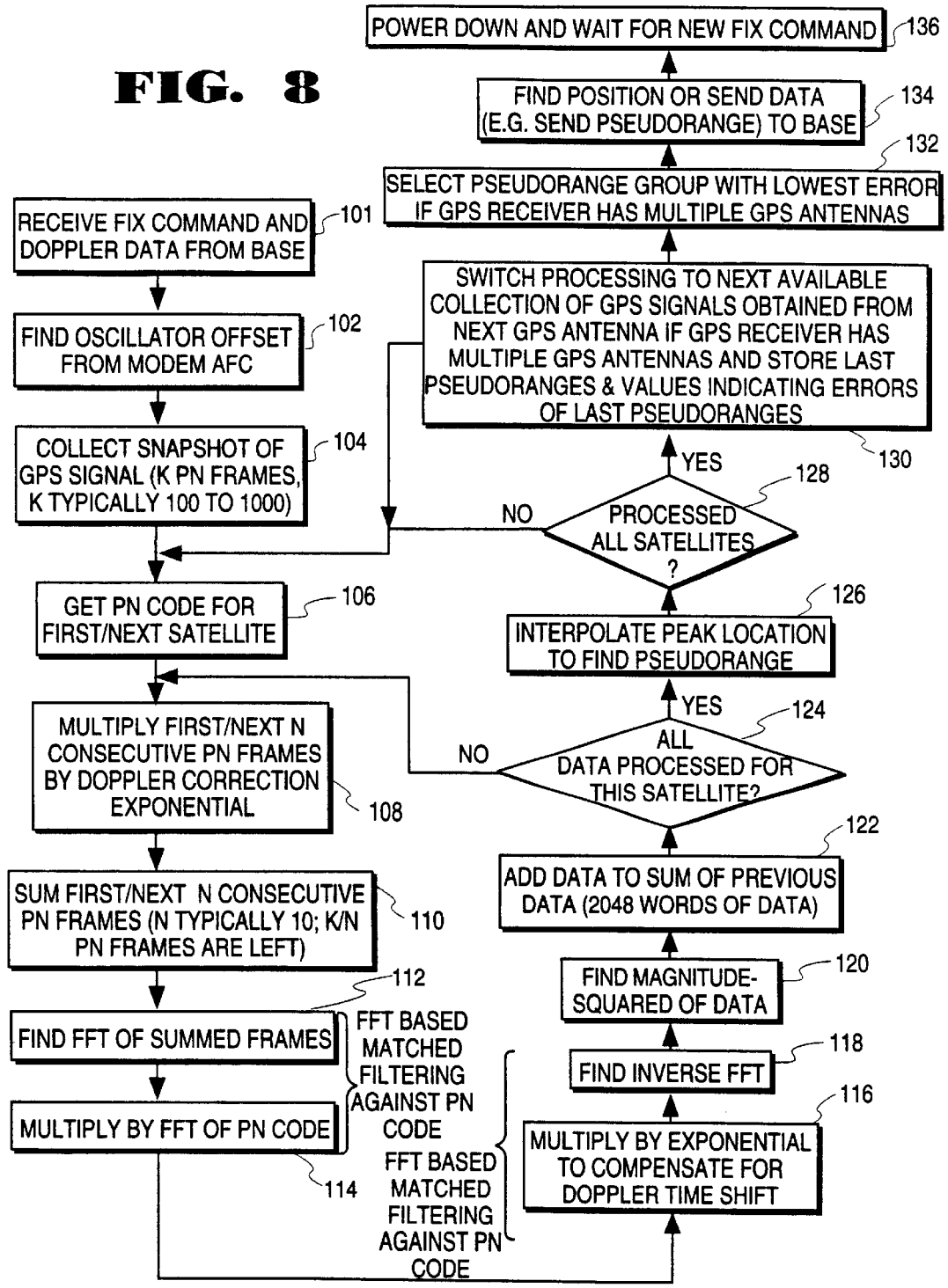
FIG. 8 is a flow chart which indicates the major operations performed by the digital processor in accordance with a typical embodiment of the present invention.

Details of the signal processing performed in the processor 10 may be understood with the aid of the flow chart of FIG. 8 and the pictorial of FIGS. 9A, 9B, 9C, 9D and 9E. It will be apparent to those skilled in the art that the machine code, or other suitable code, for performing the signal processing to be described is stored in memory 19. Suitable code for controlling reception and transmission of communication signals through a communication link (such as, for example, a two-way pager system) may also be stored in program memory 19. Other non-volatile storage devices could also be used. The objective of the GPS processing is to determine the timing of the received waveform with respect to a locally generated waveform. Furthermore, in order to achieve high sensitivity, a very long portion of such a waveform, typically 100 milliseconds to 1 second, is processed.

In order to understand the processing, one first notes that each received GPS signal (C/A mode) is constructed from a high (1 MH) repetitive pseudorandom (PN) pattern of 1023 symbols, commonly called "chips". These "chips" resemble the waveform shown in FIG. 9A. Further imposed on this pattern is low rate data, transmitted from the satellite at 50 baud. All of this data is received at a very low signal-to-noise ratio as measured in a 2 MHz bandwidth. If the carrier frequency and all data rates were known to great precision, and no data were present, then the signal-to-noise ratio could be greatly improved, and the data greatly reduced, by adding to one another successive frames. For example, there are 1000 PN frames over a period of 1 second. The first such frame could be coherently added to the next frame, the result added to the third frame, etc. The result would be a signal having a duration of 1023 chips. The phasing of this sequence could then be compared to a local reference sequence to determine the relative timing between the two, thus establishing the so-called pseudorange.

The above process is typically carried out separately for each satellite in view from the same set of stored received data in the digital memory 9, since, in general, the GPS signals from different satellites have different Doppler frequencies and the PN patterns differ from one another.

The above process is made difficult by the fact that the carrier frequency may be unknown by in excess of 5 kHz due to signal Doppler uncertainty and by an additional amount due to receiver local oscillator uncertainty. These Doppler uncertainties are removed in one embodiment of the present invention by transmission of such information from a basestation 17 which simultaneously monitors all GPS signals from in view satellites. Thus, Doppler search is avoided at the remote unit 100. The local oscillator uncertainty is also greatly reduced (to perhaps 50 Hz) by the AFC operation performed using the basestation to mobile unit communication signal (and its precision carrier frequency signal), as described in copending applications which have been incorporated herein by reference.

The presence of 50 baud data superimposed on the GPS signal limits the coherent summation of PN frames beyond a period of 20 msec. That is, at most 20 frames may be coherently added before data sign inversions prevent further processing gain. Additional processing gain may be achieved through matched filtering and summation of the magnitudes (or squares of magnitudes) of the frames, as detailed in the following paragraphs.

Figure 10:
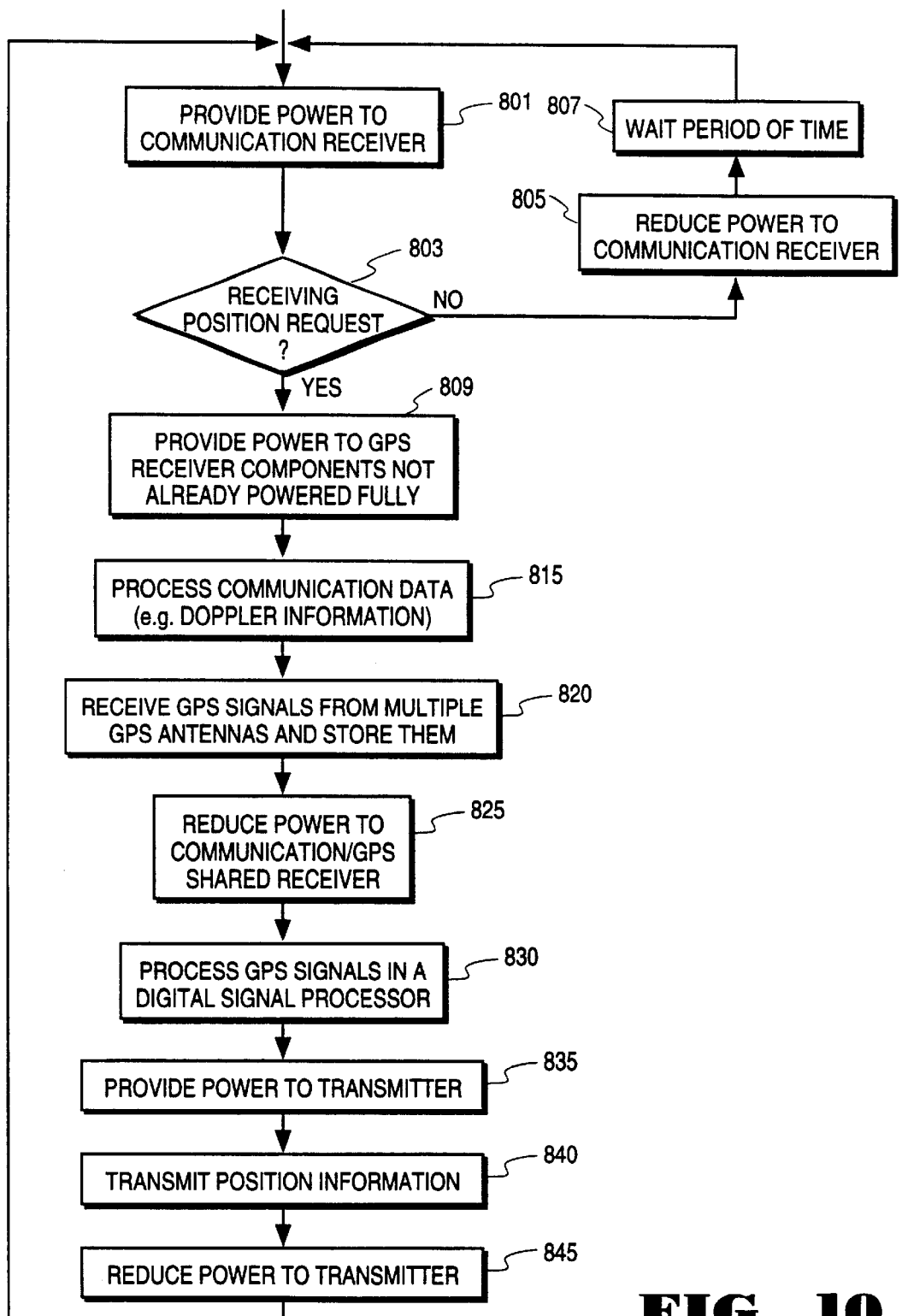
FIG. 10 is a flowchart which illustrates various steps involved in managing power consumption in a GPS receiver according to one embodiment of the present invention.

The flow chart of FIG. 8 begins at step 101 with a command from the basestation 17 to initialize a GPS processing operation (termed a "Fix Command" in FIG. 8). This command includes (in one embodiment) sending, over a communication link 14a, the Doppler shifts for each satellite in view and an identification of those satellites. At step 102, the remote units 100 computes its local oscillator drift by frequency locking to the signal transmitted from the basestation 17. An alternative would be to utilize a very good quality temperature compensated crystal oscillator in the remote unit. For example, digitally controlled TCXOs, so called DCXOs, currently can achieve accuracy of about 0.1 parts per million, or an error of about 150 Hz for the L1 GPS signal At step 104 the remote unit's processor 10 collects, from a particular GPS antenna, a snapshot of data of duration K PN frames of the C/A code, where K is typically 100 to 1000 (corresponding to 100 msec to 1 second time duration). The remote unit will, in those embodiments using multiple GPS antennas, collect a similar amount of data from each GPS antenna and store the digitized samples in the memory 9. When a sufficient amount of data has been collected, the processor 10 may reduce power consumed by the RF to IF converter 7 and the A/D converters 8 by placing these components in a reduced power state for at least a period of time (e.g. a short predetermined period of time). After this period of time, full power is typically provided again to these components in order to detect whether communication signals are being transmitted to the remote/mobile unit 100. This cycle of reduced and full power may be repeated as shown in FIG. 10 which is discussed below.

The pseudorange of each satellite is computed in turn as follows. First, at step 106 for the given GPS satellite signal to be processed, the corresponding pseudorandom code (PN) is retrieved from memory 19. As discussed shortly, the preferred PN storage format is actually the Fourier transform of this PN code, sampled at a rate of 2048 samples per the 1023 PN bits.

The data in snapshot memory 9 is processed in blocks of N consecutive PN frames, that is blocks of 2048N complex samples (N is an integer typically in the range of 5 to 10). Similar operations are performed on each block as shown in the bottom loop (steps 108–124) of FIG. 8. That is, the loop is performed a total of K/N times for each GPS signal to be processed.

At step 108 the 2048N data words of the block are multiplied by a complex exponential that removes the effects of Doppler on the signal carrier, as well as the effects of drifting of the receiver's local oscillator. To illustrate, suppose the Doppler frequency transmitted from the base station 17 plus local oscillator offsets corresponded to $f_e$ Hz. Then the premultiplication of the data would take the form of the function $e^{-j2\pi f_e nT}$, n=[0, 1, 2 . . . 2048N−1]+(B−1)× 2048 N, where T=½.048 MHz is the sampling period, and the block number B ranges from 1 to K/N.

Next, a step 110, the adjacent groups of N (typically 10) frames of data within the block are coherently added to one another. That is, samples 0, 2048, 4096, . . . 2048(N−1) −1 are added together, then 1,2049,4097.... 2048(N−1) are added together, etc. At this point the block contains only 2048 complex samples. An example of the waveform produced by such a summing operation is illustrated in FIG. 9B for the case of 4 PN frames. This summing operation may be considered a preprocessing operation which precedes the fast convolution operations.

Next, at steps 112–118, each of the averaged frames undergoes a matched filtering operation, whose purpose is to determine the relative timing between the received PN code contained within the block of data and a locally generated PN reference signal. Simultaneously, the effects of Doppler on the sampling times is also compensated for. These operations are greatly speeded, in one embodiment, by the use of fast convolution operations such as Fast Fourier Transform algorithms used in a manner to perform circular convolution, as presently described.

In order to simplify discussion, the above mentioned Doppler compensation is initially neglected.

The basic operation to be performed is a comparison of the data in the block being processed (2048 complex samples) to a similar reference PN block stored locally. The comparison is actually done by (complex) multiplying each element of the data block by the corresponding element of the reference and summing the results. This comparison is termed a "correlation". However, an individual correlation is only done for one particular starting time of the data block, whereas there are 2048 possible positions that might provide a better match. The set of all correlation operations for all possible starting positions is termed a "matched filtering" operation. The full matched filtering operation is required in a preferred embodiment.

The other times of the PN block can be tested by circularly shifting the PN reference and reperforming the same operation. That is, if the PN code is denoted p(0) p(1) . . . p(2047), then a circular shift by one is p(1) p(2) . . . p(2047) p(0). This modified sequence tests to determine if the data block contains a PN signal beginning with sample p(1). Similarly the data block may begin with samples p(2), p(3), etc., and each may be tested by circularly shifting the reference PN and reperforming the tests. It should be apparent that a complete set of tests would require 2048×2048= 4,194,304 operations, each requiring a complex multiplication and addition.

A more efficient, mathematically equivalent method may be employed, utilizing the Fast Fourier Transform (FFT), which only requires approximately 12×2048 complex multiplications and twice the number of additions. In this method, the FFT is taken for the data block, at step 112, and for the PN block The FFT of the data block is multiplied by the complex conjugate of the FFT of the reference, at step 114, and the results are inverse Fourier transformed at step 118. The resulting data so gotten is the length 2048 and contains the set of correlations of the data block and the PN block for all possible positions. Each forward or inverse FFT operation requires P/2 $\log_2$ P operations, where P is the size of the data being transformed (assuming a radix-2 FFT algorithm is employed). For the case of interest, P=2048, so that each FFT requires 11×1024 complex multiplications. However, if the FFT of the PN sequence is prestored in memory 19, as in a preferred embodiment, then its FFT need not be computed during the filtering process. The total number of complex multiplies for the forward FFT, inverse FFT and the product of the FFTs is thus (2×11+2)×1024= 24576, which is a savings of a factor of 171 over direct correlation. FIG. 9 illustrates the waveform produced by this matched filtering operation.

The preferred method of the current invention utilizes a sample rate such that 2048 samples of data were taken over the PN period of 1023 chips. This allows the use of FFT algorithms of length 2048. It is known that FFT algorithms that are a power of 2, or 4, are normally much more efficient than those of other sizes (and 2048=$2^{11}$). Hence the sampling rate so chosen significantly improves the processing speed. It is preferable that the number of the FFT equal the number of samples for one PN frame so that proper circular convolution may be achieved. That is, this condition allows the test of the data block against all circularly shifted versions of the PN code, as discussed above. A set of alternative methods, known in the art as "overlap save" or "overlap add" convolution may be utilized if the FFT size is chosen to span a number of samples different from that of one PN frame length. These approaches require approximately twice the number of computations as described above for the preferred implementation.

It should be apparent to one skilled in the art how the above process may be modified by utilizing a variety of FFT algorithms of varying sizes together with a variety of sample rates to provide fast convolution operations. In addition, a set of fast convolution algorithms exist which also have the property that the number of computations required are proportional to P $\log_2$P rather than $P^2$ as is required in straightforward correlation. Many of these algorithms are enumerated in standard references, for example, H. J. Nussbaumer, "Fast Fourier Transform and Convolution Algorithms," New York, Springer-Verlag, C1982. Important examples of such algorithms are the Agarwal-Cooley Algorithm, the split nesting algorithm, recursive polynomial nesting algorithm and the Winograd-Fourier algorithm, the first three of which are used to perform convolution and the latter used to perform a Fourier transform These algorithms may be employed in substitution of the preferred method presented above.

The method of time Doppler compensation employed at step 116 is now explained. In the preferred implementation, the sample rate utilized may not correspond exactly to 2048 samples per PN frame due to Doppler effects on the received GPS signal as well as local oscillator instabilities. For example, it is known that the Doppler shift can contribute a delay error of ±2700 nsec/sec. In order to compensate for this effect, the blocks of data processed in the above description need to be time shifted to compensate for this error. As an example, if the block size processed corresponds to 5 PN frames (5 msec), then the time shift from one block to another could be as much as ±13.5 nsec. Smaller time shifts result from local oscillator instability. These shifts may be compensated for by time shifting the successive blocks of data by multiples of the time shift required by a single block. That is, if the Doppler time shift per block is d, then the blocks are time shifted by nd, n=0, 1, 2, . . .

In general these time shifts are fractions of a sample. Performing these operations directly using digital signal processing methods involves the use of nonintegral signal interpolation methods and results in a high computation burden. An alternative approach, that is a preferred method of the present invention, is to incorporate the processing within the fast Fourier transform functions. It is well known that a time shift of d seconds is equivalent to multiplying the Fourier Transform of a function by $e^{-j2\pi fd}$, where f is the frequency variable. Thus, the time shift may be accomplished by multiplying the FFT of the data block by $e^{-j2\pi nd/T_f}$ for n=0,1,2 . . . , 1023 and by $e^{-j2\pi(n-2048)d/T_f}$ for n=1024, 1024, . . . , 2047, where $T_f$ is the PN frame duration (1 millisecond). This compensation adds only about 8% to the processing time associated with the FFT processing. The compensation is broken into two halves in order to guarantee continuity of phase compensation across 0 Hz.

After the matched filtering operation is complete, the magnitudes, or magnitudes-squared, of the complex numbers of the block are computed at step 120. Either choice will work nearly as well. This operation removes effects of 50 Hz data phase reversals (as shown in FIG. 9D) and low frequency carrier errors that remain. The block of 2048 samples is then added to the sum of the previous blocks processed at step 122. Step 122 may be considered a post processing operation which follows the fast convolution operation provided by steps 112–118. This continues until all K/N blocks are processed, as shown by the decision block at step 124, at which time there remains one block of 2048 samples, from which a pseudorange is calculated. FIG. 9E illustrates the resulting waveform after the summing operation.

Pseudorange determination occurs at step 126. A peak is searched for above a locally computed noise level. If such a peak is found, its time of occurrence relative to the beginning of the block represents the pseudorange associated with the particular PN code and the associated GPS satellite.

An interpolation routine is utilized at step 126 to find the location of the peak to an accuracy much greater than that associated with the sample rate (2.048 MHz). The interpolation routine depends upon the prior bandpass filtering used in the RF/IF portion of the remote unit 100. A good quality filter will result in a peak having a nearly triangular shape with the width of the base equal to 4 samples. Under this condition, following subtraction of an average amplitude (to remove a DC baseline), the largest two amplitudes may be used to determine the peak position more precisely. Suppose these amplitudes are denoted $A_p$ and $A_p+1$, where $A_p \geq A_p+1$ without loss of generality, and p is the index of the peak amplitude. Then the position of the peak relative to that corresponding to Ap may be provided by the formula: peak location=$p+A_p/(A_p+A_p+1)$. For example if $A_p = A_p+1$, then the peak location is found to be p+0.5, that is, halfway between the indices of the two samples. In some situations, the bandpass filtering may round the peak and a three point polynomial interpolation may be more suitable.

In the preceding processing, a local noise reference used in thresholding, may be computed by averaging all the data in the final averaged block, after removing the several largest such peaks.

Once the pseudorange is found, the processing continues at step 128 in a similar manner for the next satellite in view, unless all such satellites have been processed. Upon completion of the processing for all such satellites, the process continues at step 130 where the system switches processing to the next unprocessed collection of GPS signals from the next GPS antenna if the GPS receiver has multiple GPS antennas. In this case of multiple antennas, processing proceeds from step 130 to step 106, and the next unprocessed collection of GPS signals is used in the loop of processing steps 106 through 128. If it is determined at step 130 that all collections of GPS signals from multiple (e.g. all or some) GPS antennas have been processed or if the GPS receiver is using only one antenna, then processing continues from step 130 to step 132. Before proceeding from step 130 to step 106, the system stores the last pseudoranges (calculated in step 126 for all processed satellites for the current collection of GPS signals) and stores a value (or values) indicating the error of these last pseudoranges. These stored values will be used later in step 132 to select a selected position information which has the lowest error. This selected position information will be transmitted (in one embodiment) to the base station 17.

At step 132, the system determines whether multiple GPS antennas have been used to collect and process different collections of GPS signals. If multiple GPS antennas have not been so used, then processing proceeds to step 134. If multiple GPS antennas have been so used, then the system determines in step 132 the selected position information. Pseudoranges are calculated for each satellite in view and for each buffered set of samples. We term the pseudoranges found for a buffered set of data a pseudorange group (PRG). Pseudoranges are selected based upon their signal-to-noise ratios (SNR's). The SNR may be computed as the signal power out of the matched filter (or correlator) divided by background noise level. The latter may be computed as the mean-squared matched filter output for delays away from the peak output. An estimate of RMS position error, (e.g. latitude and longitude) may be determined without solving the navigation equations by combining the pseudorange SNR's with the approximate positions of the satellites corresponding to such pseudoranges and the approximate position of the GPS receiver. Such methods are well known in the art and are discussed, for example, in *Global Positioning System, Theory and Applications*, Vol. I, Chapter 5, by B. W. Parkinson and J. J. Spilker (American Institute of Aeronautics and Astronautics, c1996).

Three methods for computing position from the pseudorange groups are described here:

(1) Find the pseudorange group that will result in the lowest RMS position error and compute the position from the data in that group, by means commonly used in the art. This group of pseudoranges is the selected position information.

(2) For each satellite, find the pseudorange (to that satellite) from the various groups that has the highest signal-to-noise ratio. The pseudoranges thus found (one per each satellite), become the selected position information. In this method, it is necessary to compensate for the difference in collection times of the data in the different buffers. It is assumed that the internal receiver clock keeps track of the relative times of collection of the buffers. Hence if two buffers were collected at times $T_0$ and $T_1$, then the pseudorange corresponding to the second buffer can be compensated for use with those of the first buffer by subtracting $T_1 - T_0 + (R^{SV}(T_1) - R^{SV}(T_0))/c$, where c is the speed of light and $R^{SV}(T)$ is the approximate range at time T of the satellite in question. The latter quantity can be predicted if the position of the GPS receiver is known (e.g. to 100 mile radius), the approximate time of day is known, and the approximate satellite positions are known (e.g. via the Almanac of the GPS constellation). This compensation also assumes that the local clock is known very accurately, e.g. by subtracting the predicted Doppler (via the Almanac) and the measured Doppler associated with the first pseudorange. Alternatively, this quantity may be measured directly from the received signal's Doppler, if the local clock is accurate. The pseudoranges thus found and corrected can be used to compute position by means commonly used in the art.

(3) Combine all the pseudorange data from the several buffers and compute position based upon all this data In this approach, the pseudorange data is corrected for buffer time displacement, as in the previous approach (number 2). Then a least-mean-square (LMS) fit is utilized to determine position, where the signal-to-noise ratios of each of the pseudoranges is used as weighting elements in the LMS performance index (pseudoranges with poorer SNR's are weighted less).

The three methods above may be implemented either at the GPS receiver, or at a remote basestation, if the pseudoranges, collection times, and SNR's are transferred to the basestation over a suitable data link. In the latter case, methods (1) and (2) require less data transfer than method (3).

There are various combinations and simplifications of the above methods. For example, method 1 can be utilized by only selecting the group that has the best RMS SNR, without regard to satellite positions.

Then the process continues in step 134 where the pseudorange data is transmitted to the base station 17 over a communication link 14a. The final position calculation of the remote unit 100 is performed by the base station in an embodiment of the invention where the base station computes a latitude and longitude rather than the mobile unit 100. Finally, at step 136, at least some of the circuitry of the remote 100 (e.g. modulator 1, converter 12 and amplifier 13) is placed in a low power state awaiting a new command to perform another positioning operation.

A summary of the signal processing described above and shown in FIG. 8 will now be provided. The GPS signals from one or more in view GPS satellites are received at the remote GPS unit using a GPS antenna or multiple GPS antennas in those embodiments which use multiple GPS antennas. These signals are digitized and stored in a buffer in the remote GPS unit. After storing these signals from a particular GPS antenna, a processor performs preprocessing, fast convolution processing, and post processing operations on these signals. In the case where the GPS receiver has multiple GPS antennas which collect multiple groups of GPS signals (where each group is obtained from one particular GPS antenna), these processing operations (pre-processing, fast convolution, and post-processing) are performed separately on each group of GPS signals from one particular GPS antenna These processing operations involve:

a) breaking the stored data into a series of consecutive (e.g., non-contiguous or contiguous) blocks whose durations are equal to a multiple of the frame period of the pseudorandom (PN) codes contained within the GPS signals.
  b) for each block performing a preprocessing step which creates a compressed block of data with length equal to the duration of a pseudorandom code period by coherently adding together successive subblocks of data, the subblocks having a duration equal to one PN frame; this addition step will mean that the corresponding sample numbers of each of the subblocks are added to one another.
  c) For each compressed block, performing a matched filtering operation, which utilizes fast convolution techniques, to determine the relative timing between the received PN code contained within the block of data and a locally generated PN reference signal (e.g. the pseudorandom sequence of the GPS satellite being processed).
  d) Determining a pseudorange by performing a magnitude-squared operation on the products created from said matched filtering operation and post processing this by combining the magnitude-squared data for all blocks into a single block of data by adding together the blocks of magnitude-squared data to produce a peak.
  and
  e) finding the location of the peak of said single block of data to high precision using digital interpolation methods, where the location is the distance from the beginning of the data block to the said peak, and the location represents a pseudorange to a GPS satellite corresponding to the pseudorandom sequence being processed.

Typically, the fast convolution techniques used in processing the buffered GPS signals is a Fast Fourier Transform (FFT) and the result of the convolution is produced by computing the product of the forward transform of the compressed block and a prestored representation of the forward transform of the pseudorandom sequence to produce a first result and then performing an inverse transformation of the first result to recover the result. Also, the effects the Doppler induced time delays and local oscillator induced time errors are compensated for on each compressed block of data by inserting between the forward and inverse Fast Fourier Transform operation, the multiplication of the forward FFT of the compressed blocks by a complex exponential whose phase verses sample number is adjusted to correspond to the delay compensation required for the block.

In the foregoing embodiment the processing of GPS signals from each satellite occurs sequentially over time, rather than in parallel. In an alternative embodiment, the GPS signals from all in view satellites may be processed together in a parallel fashion in time.

It is assumed here that the base station 17 has a common view of all satellites of interest and that it is sufficiently close in range to remote unit 100 in order to avoid ambiguities associated with the repetition period of the C/A PN code. A range of 90 miles will satisfy the criteria The base station 17 is also assumed to have a GPS receiver and a good geographical location such that all satellites in view are continuously tracked to high precision.

While several described embodiments of the base station 17 show the use of a data processing component, such as a computer at the base station in order to compute position information such as a latitude and a longitude for the mobile GPS unit, it will be appreciated that each base station 17 may merely relay the information received, such as pseudoranges from a mobile GPS unit, to a central location or several central locations which actually perform the computation of latitude and longitude. In this manner the cost and complexity of these relaying base stations may be reduced.

Figure 7:
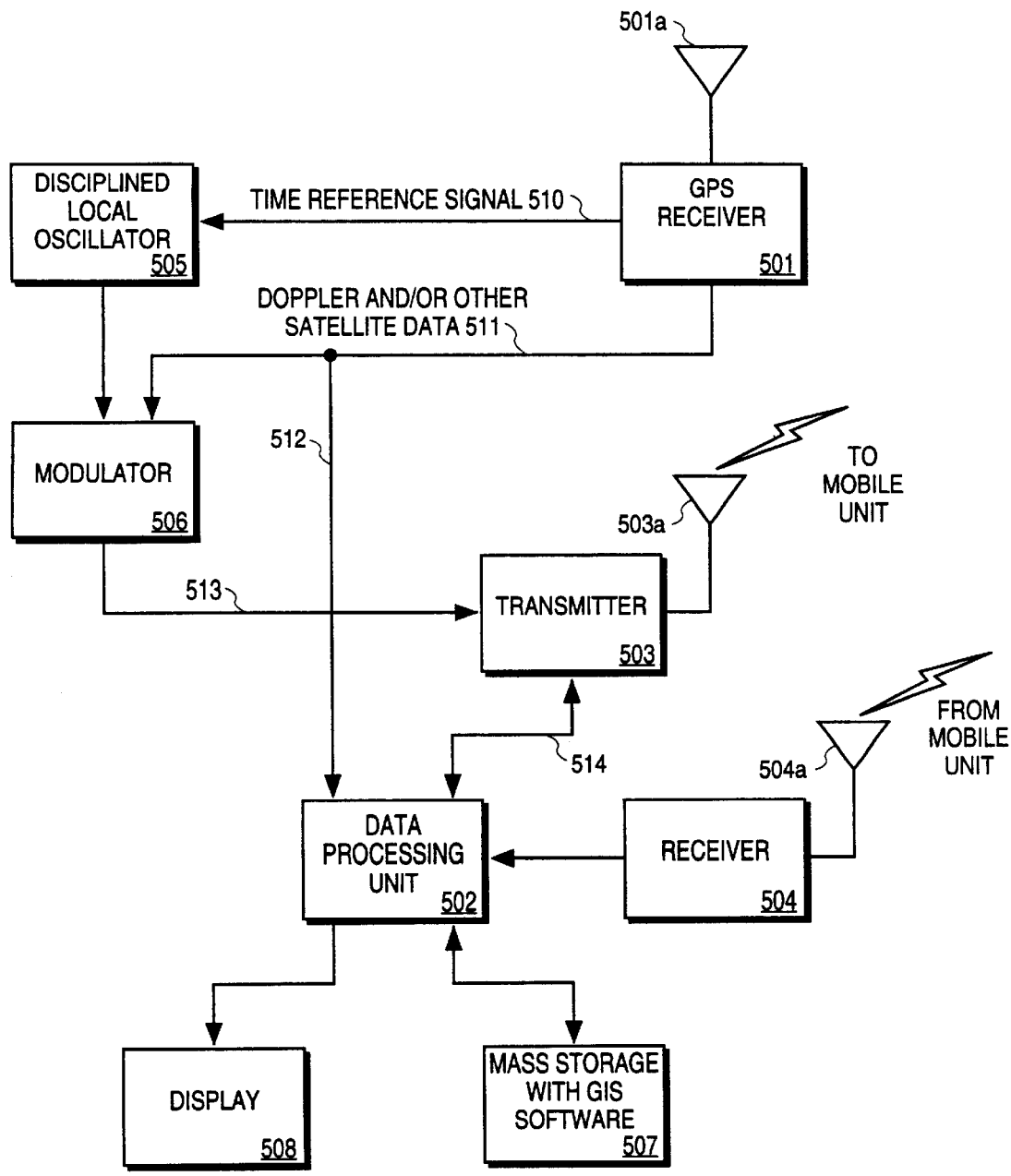
FIG. 7 shows an example of a base station according to the present invention which may be utilized with a GPS receiver of the present invention.

FIG. 7 shows one embodiment of a base station used according to the present invention. In this base station, a GPS receiver 501 receives GPS signals through a GPS antenna 501A. The GPS receiver 501, which may be a conventional GPS receiver, provides a timed reference signal which is typically timed relative to GPS signals and also provides Doppler information relative to the satellites in view. This GPS receiver 501 is coupled to a disciplined local oscillator 505 which receives the time reference signal 510 and phase locks itself to this reference. This disciplined local oscillator has an output which is provided to a modulator 506. The modulator 506 also receives Doppler data information signals for each satellite in view of the GPS mobile unit, such as the unit 100, and/or other satellite data information signals (e.g., data representative of satellite ephemeris via interconnect 511.) The modulator 506 modulates the Doppler and/or other satellite data information onto the local oscillator signal received from the disciplined local oscillator 505 in order to provide a modulated signal 513 to the transmitter 503. The transmitter 503 is coupled to the data processing unit 502 via interconnect 514 such that the data processing unit may control the operation of the transmitter 503 in order to cause the transmission of satellite data information, such as Doppler information to a GPS mobile unit (e.g., remote unit 100 having shared circuitry) via the transmitter's antenna 503a. In this manner, a GPS mobile unit may receive the Doppler information, the source of which is the GPS receiver 501 and may also receive a high precision local oscillator carrier signal which may be used to calibrate the local oscillators in the GPS mobile unit.

The base station as shown in FIG. 7 also includes a receiver 504 which is coupled to receive communication signals from the remote unit, such as unit 100, via a communication antenna 504A. It will be appreciated that the antenna 504A may be the same antenna as the transmitter's antenna 503A such that a single antenna serves both the transmitter and the receiver in the conventional fashion. The receiver 504 is coupled to the data processing unit 502 which may be a conventional computer system. The processing unit 502 may also include an interconnect 512 to receive the Doppler and/or other satellite data information from the GPS receiver 511. This information may be utilized in processing pseudorange information or other information received from the mobile unit containing the GPS system of the present invention, such as unit 100 or 201, or 201A or 100A or 100B. This data processing unit 502 is coupled to a display device 508, which may be a conventional CRT. The data processing unit 502 is also coupled to a mass storage device 507 which includes geographical information system software which is used to display maps on the display 508. Using the displayed maps, the position of the mobile GPS unit, such as unit 100 may be indicated on the display relative to a displayed map such that the position of the object having the GPS unit may be tracked as described below.

Figure 4:
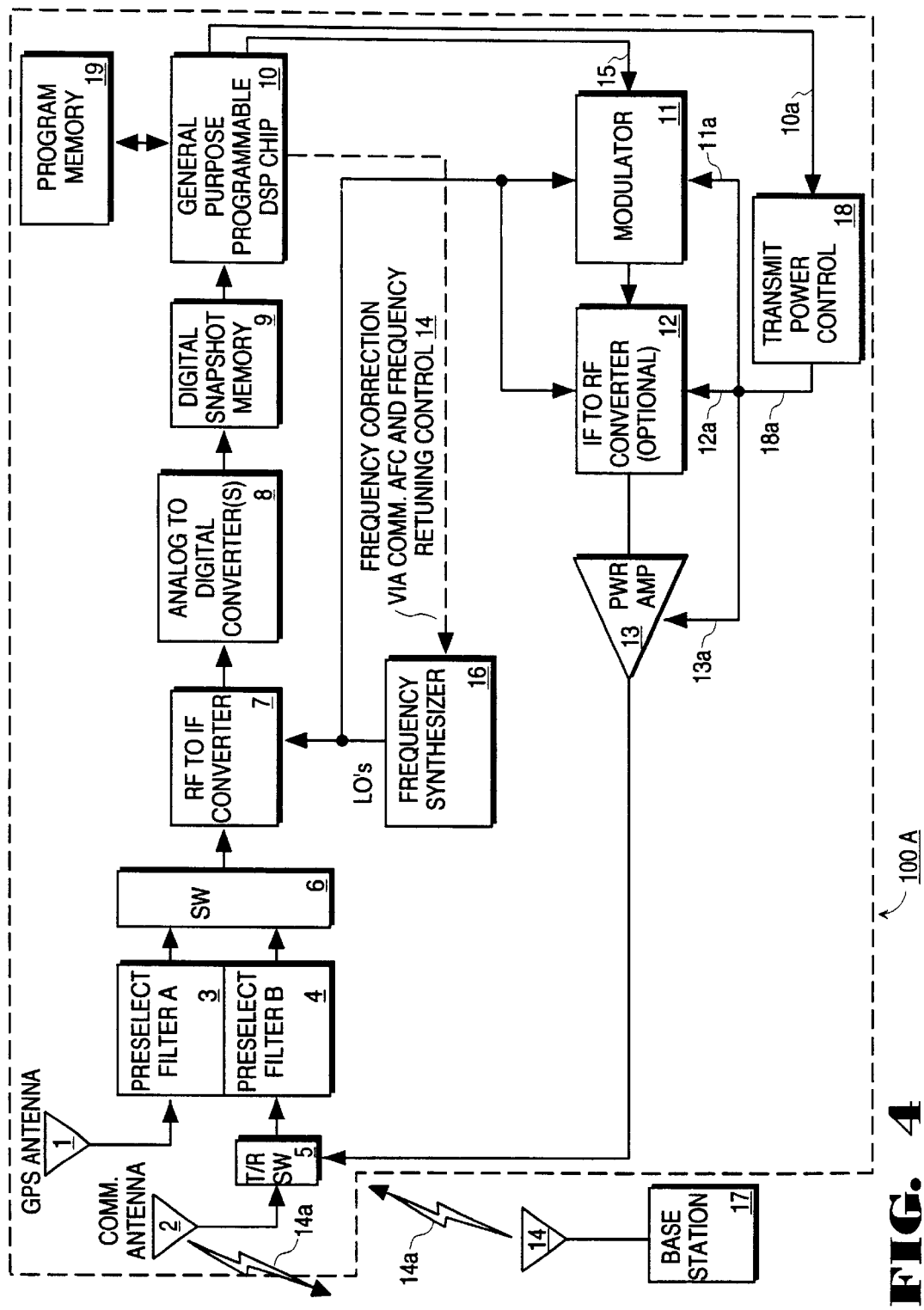
FIG. 4 is a block diagram of major components of a mobile combined system having a GPS reception as well as a communications system which can establish a communication with a base station.
Figure 5A:
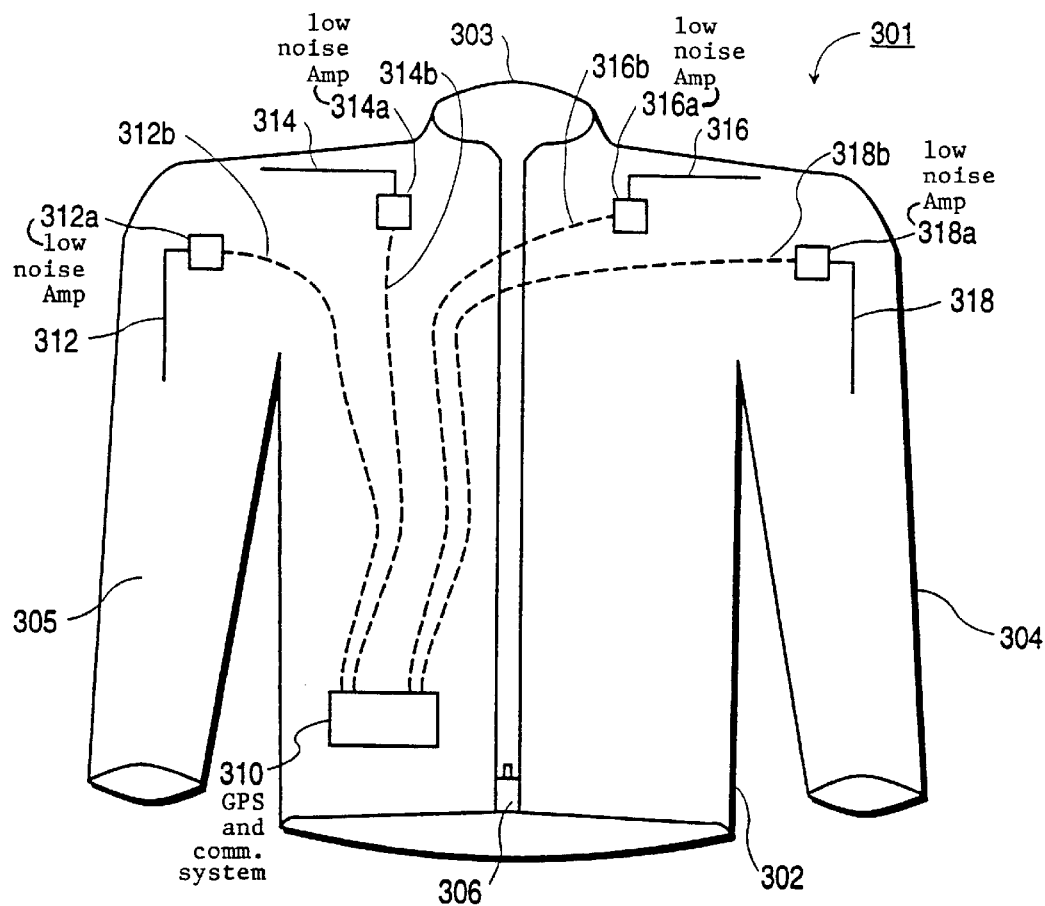
FIGS. 5A and 5B illustrate two garments according to the present invention.

Another aspect of the present invention which relates to a garment of the present invention will now be described. Two such garments are shown as examples in FIGS. 5A and 5B. FIG. 5A shows a jacket 301 of the present invention. The jacket 301 includes a main body portion 302 which encircles and encloses the chest of the wearer of the jacket as well as a collar 303 and sleeves 304 and 305. The jacket may be closed by using the zipper 306 on the front of the jacket. The jacket may be made from conventional materials including cloth, leather, etc. The jacket includes, in one embodiment, the GPS receiver and communication system 310 integrated into the jacket as well as several GPS antennas and a communication antenna which are part of the jacket. The GPS receiver and communication system 310 may be any one of the GPS receiver and communication systems described herein, including those systems shown in FIGS. 1A, 2A, 3, or FIG. 4 as well as variations of these systems described. In the case of the system shown in FIG. 4, the jacket will include only one GPS antenna which is used by the GPS receiver, but in all other cases, the GPS receiver may utilize the multiple GPS antennas which are typically embedded into the jacket In other embodiments, the GPS antenna, or GPS antennas, may be attached to (or otherwise integrated into) the garment while the GPS receiver and communication system may be attached to another object, such as a belt or holster, which is near the garment. In this case, the GPS receiver and communication system are coupled to their respective antennas on the garment, although the communication antenna may be part of (and attached to) the communication system rather than being attached to the garment.

As shown in FIG. 5A, the jacket includes GPS antennas 312, 314, and 318 which are respectively shown on the right arm sleeve, the right shoulder, and the left arm sleeve of the jacket Each of these GPS antennas is coupled to a low noise amplifier (amplifiers 312A, 314A and 318A) which provides amplified GPS signals to the unit 310 via flexible wiring lines 312B, 314B, and 318B, respectively. It will be appreciated that these amplifiers 312A, 314A, and 318A are similar to the amplifiers 24 and 25 shown in FIG. 1A. As shown in FIG. 5A, each amplifier is located adjacent to its corresponding GPS antenna to which it is coupled and each amplifier is coupled to the unit 312 via conductor which is typically a flexible conductor or conductors. Often, the antenna will be located a distance away (e.g. a foot away or further away) from the GPS receiver and communication unit 310.

A communication antenna 316 having an associated low noise amplifier (on the reception side only) 316A is shown coupled to the unit 310 by another flexible conductor 316B. The communication antenna is coupled to (in a typical embodiment) a communication transmitter which is also coupled to the GPS receiver. This allows the GPS receiver after calculating certain position information to transmit though the communication transmitter and through the communication antenna the position information back to the base station thereby allowing the wearer of the garment to be tracked at the base station.

In a typical embodiment, the multiple GPS antennas will be strip antennas which are substantially coplanar with the surface of a garment and are typically concealed in or on the garment and are attached to the garment by sewing. Thus, the GPS antenna will not protrude from the garment and will often be an inconspicuous part of the garment Also in a typical embodiment, the GPS receiver and communication system 310 will employ the low power management techniques of the present invention in order to conserve battery power and allow the unit to carry fewer or less heavy batteries such that the garment is not uncomfortable to wear. The unit 310 typically also includes a communication receiver which receives GPS positioning commands which can cause the GPS receiver to determine position information. The communication receiver can also receive satellite information such as Doppler information relative to the satellites in view.

The GPS antenna (or GPS antennas) may be attached to the garment by velcro, sewing, buttons or a zipper. Similarly, the GPS receiver and/or the communication system may be attached to the garment by velcro, sewing, buttons or a zipper.

The garment of the present invention may be used with a method of tracking which is another aspect of the present invention.

It will be appreciated that this garment may be worn by a person or object in order to track the person or object This person may be a soldier, a policeman, a firefighter, emergency response personnel, a child, an Alzheimer patient, an epileptic patient, a person with a medical condition, a field personnel, (e.g., a delivery personnel or a repair service personnel or other field service personnel) or a criminal or individuals under court order. Alternatively, the object being tracked may be a vehicle or a animal or some other movable object (e.g. an asset such as cargo). In a typical implementation in the method of tracking the object, the method includes the steps of receiving at the object a positioning command. In a normal implementation the receipt of this positioning command occurs by a receiver in the unit 310 receiving remotely transmitted GPS positioning commands to the unit 310. Alternatively, unit 310 may generate the positioning command at the object without any transmission of the command from a station remote from the object. This would typically occur in situations where the user or wearer would activate a switch upon the occurrence of a panic condition or a medical emergency. Upon receiving the positioning command, the GPS receiver unit would then receive GPS signals through a first GPS antenna on the object and store digitized samples of these first GPS signals in a digital memory at the object Then a processor such as a digital processor at the object would process the first digitized samples by performing fast convolutions as described herein. Then, the position information computed by the processor would be transmitted by the communication transmitter at the object from the object to a station remote from the object. The station which is remote from the object is typically a base station such as that shown in FIG. 7 which can display the position of the object relative to a map and thereby allow the unit to be tracked over time by repeatedly receiving position information from object.

Figure 5B:
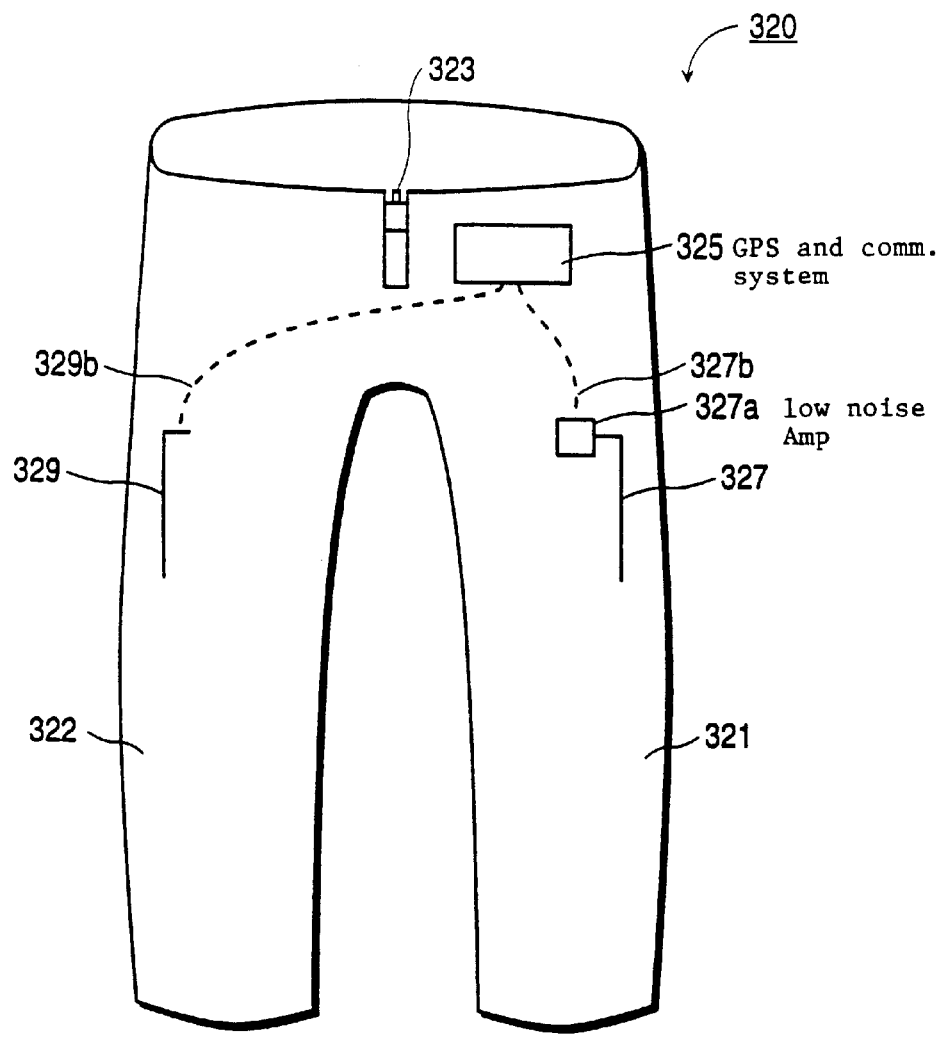

FIG. 5B shows another garment of the present invention; specifically, it shows pants 320 which may be worn by a person. The pants include legs 321 and 322 as well as a zipper 323. They also include a GPS receiver and communications system 325 which may be the system shown in FIG. 4 herein. Further details regarding the system shown in FIG. 4, which is a single GPS antenna embodiment having shared/common circuitry (shared between the communications system and the GPS receiving system) is described in copending application Ser. No. 08/652,833 filed on May 23, 1996, and entitled Combined GPS Positioning System and Communications System Utilizing Shared Circuitry, by Norman F. Krasner, which application is hereby incorporated herein by reference.

The garment of FIG. 5B includes a GPS antenna 327 which is coupled to the unit 325 by a low noise amplifier 327A and flexible conductor 327B. The garment 320 also includes a communication antenna 329, which is coupled to the unit 325 by flexible conductor 329B.

It will be appreciated that numerous alternative embodiments of the garment of the present invention may be created. For example, the garment may be a glove or a belt or a shoe or other types of pants or jackets or shirt other types of clothing which encircle and enclose portions of the wearer's body. In addition, the communication transmitter and/or communication receiver may be placed away from the garment rather than being part of the garment; for example, such transmitter or receiver may be placed on a belt clip or in a holster.

A method of conserving and reducing power consumption in a GPS receiver and communications system will now be described. A particular example of this method is shown in FIG. 10. This method typically operates by the processor 10 controlling power reduction under control of a program stored in memory 19. Alternatively, a separate power management logic circuit may control power reduction; an example of this embodiment is shown in FIG. 2A. The method shown in FIG. 10 will be described for the system shown in FIG. 1A. Power reduction is typically achieved by controlling power interconnects to various components. For example, the transmitter section receives power controlled interconnects through a transmit power control 18 as shown in FIG. 1A. Similarly, the receiver section may receive power through power controlled interconnects (not shown) which provide power to components (e.g. converter 7 and 8) in the shared receiver section. It will be appreciated that in some applications power may be provided without interruption to the reference oscillators and phase lock loops in the frequency synthesizer since these components require some time to stabilize after power is first provided to them. The method begins in step 801 where fill power is provided to the communication receiver, this receiver includes the RF to IF converter 7 and the A/D converter 8 in the preselect filter 4. Any communication signals received during this time are stored in memory 9 and demodulated by processor 10.

The processor 10 determines in step 803 whether the communication signals received during step 801 include a request to provide position information of the combined system 100 shown in FIG. 1A. This request is also referred to as a fix command. If no such request is received, power to the communication receiver is reduced in step 805 and the processor 10, in step 807, waits a period of time ( e.g., a predetermined period of time) before returning to step 801. If such a request is received, the processor 10 causes, in step 809, full power to be provided to components of the GPS/communication receiver which have not already received full power; an example such components includes preselect filter 3 (which may include a low noise amplifier) which may remain in a reduced power state while the communication signals are received. The processor 10, in step 815, processes any communication data received by the communication receiving operation. Such data may include satellite Doppler information for satellites in view and identification of these satellites. Then in step 820, the GPS receiver of the shared GPS/communication receiver shown in FIG. 1A receives the GPS signals from the satellites in view and digitized versions of the signals are stored in memory 9. Step 820 is repeated for each group of GPS signals from each GPS antenna when the system includes multiple GPS antennas. Processor 10 then causes the power consumed by the shared GPS/communication receiver (e.g. converter 7 and 8) to be reduced in step 825 and in step 830, the processor 10 processes the stored GPS signals. After the processor determines the position information (e.g. pseudoranges to a plurality of satellites in view or a latitude and longitude of the system), the processor 10 causes, in step 835, power to be provided to the transmitter section by instructing the power control 18 to provide full power to the modulator 11, converter 12 and power amplifier 13. Then the transmitter in step 840 transmits the position information and then, in step 845, power provided to the transmitter section is reduced. Processing then returns back to step 801 to continue from this point In the foregoing specification, the invention has been described with reference to specific exemplary embodiments thereof. It will however be evident that various modifications and changes may be made thereto without departing from the broader spirit and scope of the invention as set forth in the pending claims. The specification and drawings are, accordingly, to be regarded in an illustrative sense rather than a restrictive sense.

We claim:

1. A garment comprising:
   a first GPS antenna attached to said garment;
   a communication antenna attached to said garment;
   a GPS receiver coupled to said first GPS antenna;
   a communication transceiver coupled to said communication antenna and to said GPS receiver wherein said communication transceiver is configured to transmit a position information from said GPS receiver through said communication antenna to a remote site in response to an activation signal received by said communication transceiver.

2. A garment comprising:
   a first GPS antenna attached to said garment;
   a communication antenna attached to said garment;
   a GPS receiver coupled to said first GPS antenna;
   a communication transmitter coupled to said communication antenna and coupled to said GPS receiver;
   a second GPS antenna attached to said garment, wherein said second GPS antenna is coupled to said GPS receiver.

3. A garment comprising:

a first GPS antenna attached to said garment;

a communication antenna attached to said garment;

a GPS receiver coupled to said first GPS antenna;

a communication transmitter coupled to said communication antenna and coupled to said GPS receiver;

wherein said first GPS antenna is an antenna which is substantially coplanar with a surface of said garment.

4. A garment as in claim 3 wherein said garment encircles and encloses a body part when said garment is worn.

5. A garment as in claim 2 wherein said first GPS antenna and said second GPS antenna each comprises an antenna which is substantially coplanar with a surface of said garment.

6. A garment as in claim 5 wherein said first GPS antenna and said second GPS antenna are attached to said garment by sewing.

7. A garment as in claim 5 wherein said first GPS antenna and said second GPS antenna are flexible.

8. A garment as in claim 1 wherein said GPS receiver comprises:

a digital memory coupled to said first GPS antenna to receive digitized signals obtained through said first GPS antenna;

a digital processor coupled to said digital memory to process said digitized signals to provide a first position information.

9. A garment as in claim 8 wherein said first position information comprises a pseudorange which is transmitted by said communication transceiver through said communication antenna.

10. A garment as in claim 9 wherein said digital processor processes said digitized signals to provide said pseudorange by performing fast convolutions.

11. A garment as in claim 10 wherein said communication transceiver comprises a communication receiver coupled to said GPS receiver, said communication receiver receiving GPS positioning commands and causing said GPS receiver to determine said pseudorange.

12. A garment as in claim 11 wherein said communication receiver also receives satellite data information.

13. A garment as in claim 12 wherein said satellite data information is used to determine said pseudorange.

14. A garment as in claim 11 wherein said first GPS antenna and said communication antenna are flexible.

15. A garment as in claim 14 further comprising a power management circuit coupled to said GPS receiver, said power management circuit reducing power consumed by said GPS receiver.

16. A garment as in claim 14 wherein said communication receiver comprises said digital processor which processes communication signals received through said communication antenna.

17. A garment as in claim 1 further comprising an amplifier coupled to said first GPS antenna and to said GPS receiver, said amplifier amplifying GPS signals received through said first antenna.

18. A garment as in claim 17 further comprising a flexible conductor coupling said amplifier to said GPS receiver, wherein said first GPS antenna is flexible and is located adjacent to said amplifier on said garment and said GPS receiver is located a distance away from said first GPS antenna.

19. A garment as in claim 11 wherein said first GPS antenna and said communication antenna are concealed on said garment.

20. A garment comprising:

a first GPS antenna attached to said garment;

a GPS receiver coupled to said first GPS antenna;

a communication transceiver coupled to said GPS receiver and coupled to a communication antenna wherein said communication transceiver is configured to transmit a position information from said GPS receiver through said communication antenna to a remote site in response to an activation signal received by said communication transceiver.

21. A garment as in claim 20 wherein said communication antenna is attached to said garment.

22. A garment as in claim 20 wherein said GPS receiver is attached to a belt located near said garment.

23. A garment as in claim 20 wherein said communication transceiver is attached to a belt located near said garment.

24. A garment as in claim 20 further comprising a second GPS antenna attached to said garment.

25. A garment as in claim 20 wherein said first GPS antenna is attached to said garment by a zipper.

26. A garment as in claim 20 wherein said first GPS antenna is attached to said garment by velcro.

27. A garment as in claim 1 wherein said garment is not a belt or a backpack.

28. A garment as in claim 3 wherein said first GPS antenna is substantially flat.

29. A garment as in claim 20 wherein said first GPS antenna is substantially flat.

* * * * *